US012558376B2

(12) United States Patent
Shaked et al.

(10) Patent No.: US 12,558,376 B2
(45) Date of Patent: Feb. 24, 2026

(54) TISSUE REPAIR BY ACTIVATED CELLS

(71) Applicant: TECHNION RESEARCH & DEVELOPMENT FOUNDATION LIMITED, Haifa (IL)

(72) Inventors: Yuval Shaked, Binyamina (IL); Michael Timaner, Nahariya (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 976 days.

(21) Appl. No.: 17/273,461

(22) PCT Filed: Aug. 29, 2019

(86) PCT No.: PCT/IL2019/050972
§ 371 (c)(1),
(2) Date: Mar. 4, 2021

(87) PCT Pub. No.: WO2020/049552
PCT Pub. Date: Mar. 12, 2020

(65) Prior Publication Data
US 2021/0338737 A1 Nov. 4, 2021

Related U.S. Application Data

(60) Provisional application No. 62/854,367, filed on May 30, 2019, provisional application No. 62/727,568, filed on Sep. 6, 2018.

(51) Int. Cl.
| | |
|---|---|
| A61K 35/28 | (2015.01) |
| A61K 31/7068 | (2006.01) |
| A61K 40/10 | (2025.01) |
| A61K 40/40 | (2025.01) |
| A61P 17/02 | (2006.01) |

(52) U.S. Cl.
CPC .......... *A61K 35/28* (2013.01); *A61K 31/7068* (2013.01); *A61K 40/10* (2025.01); *A61K 40/40* (2025.01); *A61P 17/02* (2018.01); *A61K 2239/54* (2023.05)

(58) Field of Classification Search
CPC ...... A61K 35/28; A61K 31/7068; A61P 17/02
See application file for complete search history.

(56) References Cited

U.S. PATENT DOCUMENTS

| | | | |
|---|---|---|---|
| 6,387,369 B1 | 5/2002 | Pittenger et al. | |
| 7,794,706 B2 | 9/2010 | Carpenter et al. | |
| 9,011,840 B2 * | 4/2015 | Bartholomew ......... | A61P 17/02 |
| | | | 435/363 |
| 9,511,093 B2 | 12/2016 | Gregory et al. | |

OTHER PUBLICATIONS

Nowakowski, Adam, et al. "Engineered mesenchymal stem cells as an anti-cancer trojan horse." Stem Cells and Development 25.20 (2016): 1513-1531. (Year: 2016).*
Roodhart, Jeanine ML, et al. "Mesenchymal stem cells induce resistance to chemotherapy through the release of platinum-induced fatty acids." Cancer cell 20.3 (2011): 370-383. (Year: 2011).*
Zhang, Dongshan, et al. "Paclitaxel: new uses for an old drug." Drug design, development and therapy (2014): 279-284. (Year: 2014).*
Cappella, Paolo, et al. "Cell cycle effects of gemcitabine." International journal of cancer 93.3 (2001): 401-408. (Year: 2001).*
Voloshin, Tali, et al. "Blocking IL1β pathway following paclitaxel chemotherapy slightly inhibits primary tumor growth but promotes spontaneous metastasis." Molecular cancer therapeutics 14.6 (2015): 1385-1394. (Year: 2015).*
Bonomi, A., et al. "Effect of canine mesenchymal stromal cells loaded with paclitaxel on growth of canine glioma and human glioblastoma cell lines." The Veterinary Journal 223 (2017): 41-47. (Year: 2017).*
AHFS Patient Medication Information (MedlinePlus)[Internet]. Bethesda (MD): American Society of Health-System Pharmacists, Inc. ; c2019. Cisplatin Injection; [Updated Sep. 21, 2016; Citation Date: Sep. 27, 2016]. Available from: https://medlineplus.gov/druginfo/meds/a684036.html (Year: 2016).*
AHFS Patient Medication Information (MedlinePlus)[Internet]. Bethesda (MD): American Society of Health-System Pharmacists, Inc. ; c2019. Fluorouracil Injection; [Updated Sep. 21, 2016; Citation Date: Oct. 5, 2016]. Available from: https://medlineplus.gov/druginfo/meds/a682708.html (Year: 2016).*
AHFS Patient Medication Information (MedlinePlus)[Internet]. Bethesda (MD): American Society of Health-System Pharmacists, Inc. ; c2019. Dacarbazine; [Updated Sep. 21, 2016; Citation Date: Oct. 5, 2016]. Available from: https://medlineplus.gov/druginfo/meds/a601250.html (Year: 2016).*
AHFS Patient Medication Information (MedlinePlus)[Internet]. Bethesda (MD): American Society of Health-System Pharmacists, Inc. ; c2019. Temozolomide; [Updated Sep. 21, 2016; Citation Date: Oct. 5, 2016]. Available from: https://medlineplus.gov/druginfo/med (Year: 2016).*
Bonomi, Arianna, et al. "Gemcitabine-releasing mesenchymal stromal cells inhibit in vitro proliferation of human pancreatic carcinoma cells." Cytotherapy 17.12 (2015): 1687-1695. (Year: 2015).*

(Continued)

*Primary Examiner* — Maria G Leavitt
*Assistant Examiner* — Michael Angelo Riga
(74) *Attorney, Agent, or Firm* — The Roy Gross Law Firm, LLC; Roy D. Gross

(57) ABSTRACT

The invention relates to an activating composition comprising a cell, which may be any cell type used for cell therapy, wherein the cell is activated by a chemotherapy agent. Further, there is provided an activating composition comprising a supernatant of a composition comprising a cell, which may be any cell type used for cell therapy, wherein the cell is activated by a chemotherapy agent and wherein the supernatant is used as a therapy. The invention further provides methods for treating or preventing a disease or a condition comprising the use of the activated composition.

15 Claims, 21 Drawing Sheets

(56)                    References Cited

OTHER PUBLICATIONS

Bonomi A, Ghezzi E, Pascucci L, Aralla M, Ceserani V, Pettinari L, Coccè V, Guercio A, Alessandri G, Parati E, Brini AT, Zeira O, Pessina A. Effect of canine mesenchymal stromal cells loaded with paclitaxel on growth of canine glioma and human glioblastoma cell lines. Vet J. May 2017;223:41-47. doi: 10.1016/j.tvjl.2017.05.005. Epub May 19, 2017. PMID: 28671070.

Pourjafar M, Saidijam M, Mansouri K, Ghasemibasir H, Karimi Dermani F, Najafi R. All-trans retinoic acid preconditioning enhances proliferation, angiogenesis and migration of mesenchymal stem cell in vitro and enhances wound repair in vivo. Cell Prolif. Feb. 2017;50(1):e12315. doi: 10.1111/cpr.12315. Epub Nov. 10, 2016. PMID: 27862498; PMCID: PMC6529123.

Schenk T, Stengel S, Zelent A. Unlocking the potential of retinoic acid in anticancer therapy. Br J Cancer. Nov. 25, 2014;111(11):2039-45. doi: 10.1038/bjc.2014.412. Epub Nov. 20, 2014. PMID: 25412233; PMCID: PMC4260020.

Asmana Ningrum R. Human interferon alpha-2b: a therapeutic protein for cancer treatment. Scientifica (Cairo). 2014;2014:970315. doi: 10.1155/2014/970315. Epub Mar. 10, 2014. PMID: 24741445; PMCID: PMC3967813.

Alagesan S, Brady J, Byrnes D, Fandiño J, Masterson C, McCarthy S, Laffey J, O'Toole D. Enhancement strategies for mesenchymal stem cells and related therapies. Stem Cell Res Ther. Feb. 21, 2022;13(1):75. doi: 10.1186/s13287-022-02747-w. PMID: 35189962; PMCID: PMC8860135.

Pessina A, Bonomi A, Coccè V, Invernici G, Navone S, Cavicchini L, Sisto F, Ferrari M, Viganò L, Locatelli A, Ciusani E, Cappelletti G, Cartelli D, Arnaldo C, Parati E, Marfia G, Pallini R, Falchetti ML, Alessandri G. Mesenchymal stromal cells primed with paclitaxel provide a new approach for cancer therapy. PLoS One. 2011;6(12):e28321. doi: 10.1371/journal.pone.0028321. Epub Dec. 20, 2011. PMID: 22205945; PMCID: PMC3243689.

Kang SK, Shin IS, Ko MS, Jo JY, Ra JC. Journey of mesenchymal stem cells for homing: strategies to enhance efficacy and safety of stem cell therapy. Stem Cells Int. 2012;2012:342968. doi: 10.1155/2012/342968. Epub Jun. 13, 2012. PMID: 22754575; PMCID: PMC3382267.

Mehrabani M, Najafi M, Kamarul T, Mansouri K, Iranpour M, Nematollahi MH, Ghazi-Khansari M, Sharifi AM. Deferoxamine preconditioning to restore impaired HIF-1α-mediated angiogenic mechanisms in adipose-derived stem cells from STZ-induced type 1 diabetic rats. Cell Prolif. Oct. 2015;48(5):532-49. doi: 10.1111/cpr.12209. PMID: 26332145; PMCID: PMC6495947.

Najafi R, Sharifi AM. Deferoxamine preconditioning potentiates mesenchymal stem cell homing in vitro and in streptozotocin-diabetic rats. Expert Opin Biol Ther. Jul. 2013;13(7):959-72. doi: 10.1517/14712598.2013.782390. Epub Mar. 28, 2013. PMID: 23536977.

Takayama Y, Kusamori K, Hayashi M, Tanabe N, Matsuura S, Tsujimura M, Katsumi H, Sakane T, Nishikawa M, Yamamoto A. Long-term drug modification to the surface of mesenchymal stem cells by the avidin-biotin complex method. Sci Rep. Dec. 5, 2017;7(1):16953. doi: 10.1038/s41598-017-17166-8. PMID: 29208980; PMCID: PMC5717103.

Linares GR, Chiu CT, Scheuing L, Leng Y, Liao HM, Maric D, Chuang DM. Preconditioning mesenchymal stem cells with the mood stabilizers lithium and valproic acid enhances therapeutic efficacy in a mouse model of Huntington's disease. Exp Neurol. Jul. 2016;281:81-92. doi: 10.1016/j.expneurol.2016.04.003. Epub Apr. 13, 2016. PMID: 27085395.

Khan I, Ali A, Akhter MA, Naeem N, Chotani MA, Mustafa T, Salim A. Preconditioning of mesenchymal stem cells with 2,4-dinitrophenol improves cardiac function in infarcted rats. Life Sci. Oct. 1, 2016;162:60-9. doi: 10.1016/j.lfs.2016.08.014. Epub Aug. 17, 2016. PMID: 27543341.

Sun Y, Li QF, Yan J, Hu R, Jiang H. Isoflurane Preconditioning Promotes the Survival and Migration of Bone Marrow Stromal Cells. Cell Physiol Biochem. 2015;36(4):1331-45. doi: 10.1159/000430300. PMID: 26159215.

Liu XB, Wang JA, Ji XY, Yu SP, Wei L. Preconditioning of bone marrow mesenchymal stem cells by prolyl hydroxylase Inhibition enhances cell survival and angiogenesis in vitro and after transplantation into the ischemic heart of rats. Stem Cell Res Ther. Sep. 25, 2014;5(5):111. doi: 10.1186/scrt499. PMID: 25257482; PMCID: PMC4535299.

Li D, Wang P, Li Y, Xie Z, Wang L, Su H, Deng W, Wu Y, Shen H. All-Trans Retinoic Acid Improves the Effects of Bone Marrow-Derived Mesenchymal Stem Cells on the Treatment of Ankylosing Spondylitis: An In Vitro Study. Stem Cells Int. 2015;2015:484528. doi: 10.1155/2015/484528. Epub Jun. 1, 2015. PMID: 26124839; PMCID: PMC4466433.

Lim J, Lee S, Ju H, Kim Y, Heo J, Lee HY, Choi KC, Son J, Oh YM, Kim IG, Shin DM. Valproic acid enforces the priming effect of sphingosine-1 phosphate on human mesenchymal stem cells. Int J Mol Med. Sep. 2017;40(3):739-747. doi: 10.3892/ijmm.2017.3053. Epub Jul. 3, 2017. PMID: 28677769; PMCID: PMC5547989.

Girdlestone J, Pido-Lopez J, Srivastava S, Chai J, Leaver N, Galleu A, Lombardi G, Navarrete CV. Enhancement of the immunoregulatory potency of mesenchymal stromal cells by treatment with immunosuppressive drugs. Cytotherapy. Sep. 2015;17(9):1188-99. doi: 10.1016/j.jcyt.2015.05.009. PMID: 26276002.

Wang B, Lin Y, Hu Y, Shan W, Liu S, Xu Y, Zhang H, Cai S, Yu X, Cai Z, Huang H. mTOR inhibition improves the immunomodulatory properties of human bone marrow mesenchymal stem cells by inducing COX-2 and PGE2. Stem Cell Res Ther. Dec. 29, 2017;8(1):292. doi: 10.1186/s13287-017-0744-6. PMID: 29287601; PMCID: PMC5747167.

Crisostomo PR, Wang Y, Markel TA, Wang M, Lahm T, Meldrum DR. Human mesenchymal stem cells stimulated by TNF-alpha, LPS, or hypoxia produce growth factors by an NF kappa B- but not JNK-dependent mechanism. Am J Physiol Cell Physiol. Mar. 2008;294(3):C675-82. doi: 10.1152/ajpcell.00437.2007. Epub Jan. 30, 2008. PMID: 18234850.

Gieseke F, Kruchen A, Tzaribachev N, Bentzien F, Dominici M, Müller I. Proinflammatory stimuli induce galectin-9 in human mesenchymal stromal cells to suppress T-cell proliferation. Eur J Immunol. Oct. 2013;43(10):2741-9. doi: 10.1002/eji.201343335. Epub Jul. 23, 2013. PMID: 23817958.

Zhang Q, Fu L, Liang Y, Guo Z, Wang L, Ma C, Wang H. Exosomes originating from MSCs stimulated with TGF-β and IFN-γ promote Treg differentiation. J Cell Physiol. Sep. 2018;233(9):6832-6840. doi: 10.1002/jcp.26436. Epub Apr. 11, 2018. PMID: 29336475.

Lu Z, Chen Y, Dunstan C, Roohani-Esfahani S, Zreiqat H. Priming Adipose Stem Cells with Tumor Necrosis Factor-Alpha Preconditioning Potentiates Their Exosome Efficacy for Bone Regeneration. Tissue Eng Part A. Nov. 2017;23(21-22):1212-1220. doi: 10.1089/ten.tea.2016.0548. Epub Mar. 23, 2017. PMID: 28346798.

International search report for PCT/IL2019/050972 dated Apr. 6, 2020.

Written opinion for PCT/IL2019/050972 dated Apr. 6, 2020.

* cited by examiner

Number of cells in lungs

TISSUE REPAIR BY ACTIVATED CELLS

This application is a National Phase of PCT Patent Application No. PCT/IL2019/050972 having International filing date of Aug. 29, 2019 titled "TISSUE REPAIR BY ACTIVATED CELLS", which claims the benefit of priority under 35 U.S.C. § 119 (e) of U.S. Provisional Application No. 62/727,568, filed on Sep. 6, 2018 and 62/854,367 filed on May 30, 2019. The contents of the above applications are all incorporated by reference as if fully set forth herein in their entirety.

BACKGROUND OF THE INVENTION

Tissue regeneration provides an organism with a vital ability to renew injured tissues and preserve normal organ function in aging, trauma, autoimmune disease, and malignancies, among others. Tissue repair is a complex multi-parametric process. It involves initial secretion of pro-inflammatory cytokines and chemokines in the injured site, followed by a recruitment of various mesenchymal and hematopoietic cells to the damaged tissue to protect it from the destructive inflammatory process. The process leads to an anti-inflammatory cascade, which eventually restores the integrity of the organ and regenerates the injured tissue. Therefore, the major interest of cell therapy research in the context of tissue injury and repair is focused on using different cell types with distinct anti-inflammatory and regenerative properties in order to enhance the natural tissue repair in response to the damage and the initial acute pro-inflammatory cascade. Among these cells are mesenchymal stem cells (MSCs) and macrophages.

Residing in various mesenchymal tissues, MSCs obtain strong anti-inflammatory properties by secreting factors such as IL-1RA, $PGE_2$, TSG6, and TGFβ, therefore inducing immunosuppression activity. Moreover, we and others have previously shown that MSCs specifically home to tumors or damaged tissue sites and reduce inflammation and improve vascularization and tissue repair. In addition, it was previously shown that in pancreatic cancer, chemotherapy-activated MSCs enrich and preserve cancer stem cell (CSC) niche by activating the CXCL10-CXCR3 axis and promote resistance for cytotoxic agents, leading to enhanced tumor growth and aggressiveness. Macrophages are also known to have a crucial effect on tissue homeostasis and wound healing. Being highly plastic cells, macrophages phenotypically skew from a pro-inflammatory to an anti-inflammatory "reparative" state, secreting IL-10, transforming growth factor beta (TGFβ), insulin-like growth factor-1 (IGF1), and VEGF, suppressing T cells and promoting tissue repair. Furthermore, macrophages enhance tissue regeneration and tumor growth by inducing angio- and lymphangiogenesis. Taken together, these abilities turn macrophages and MSCs into optimal targets for cell-based therapy.

Yet, despite the therapeutic potential of certain cell types to repair damaged tissue, cell therapy is still not the assigned first line of treatment. One of the main reasons for that is lack of specificity and activity of cells, therefore delaying and minimizing tissue regeneration and wound healing. In particular, current methods apply various growth factors and cytokines to activate the effector cells, such as TNFα and IFNγ. These factors have been shown to activate stromal cells contributing to tumor growth inhibition and tissue repair. In other cases, expensive genetic modifications are required for cell activation, which can also increase toxicity and immunocompatibility of the effector cells, and the efficiency of such methods is relatively low. Here, we suggest a novel, simple and cost-effective method for specific activation of different cells to induce tissue regeneration and repair.

SUMMARY OF THE INVENTION

In some embodiments of the invention, there is provided an activating composition comprising any cell type used for cell therapy that is activated by a chemotherapy agent.

In some embodiments of the invention, there is provided an activating composition comprising any cell type used for cell therapy that is activated by a chemotherapy agent, wherein the cell type used for cell therapy that is activated by a specific chemotherapy agent was separated from a conditioned media and wherein the conditioned media is used as a therapy.

In some embodiments of the invention, there is provided an activating composition comprising mesenchymal stem cells and/or macrophages or any other cell type that may be used in cell therapy that are activated by a chemotherapy agent, wherein the mesenchymal stem cells and/or the macrophages and/or the cell type that may be used in cell therapy that are activated by a specific chemotherapy agent were separated from a conditioned media and wherein the conditioned media is used as a therapy.

In some embodiments of the invention, there is provided a method for producing activated cells which may be any cell type used for cell therapy for use in tissue repair, the method comprising: activating the cell type used for cell therapy by culturing any cell type used for cell therapy with a chemotherapy agent.

In some embodiments of the invention, there is provided a method for producing activated mesenchymal stem cells and/or activated macrophages for use in tissue repair, said method comprising: activating the mesenchymal stem cells and/or the macrophages by culturing the mesenchymal stem cells and/or the macrophages with a chemotherapy agent.

In some embodiments of the invention, there is provided a method for promoting tissue regeneration or organ repair, or for reducing inflammation in a mammal, the method comprising:

(a) obtaining an activating composition of any cell type used for cell therapy that is activated by chemotherapy agent; and (b) administering the activating composition to a mammal in need of tissue regeneration, organ repair or reducing an inflammation.

In some embodiments of the invention, there is provided a method for promoting tissue regeneration or organ repair, or for reducing inflammation in a mammal, the method comprising:

(a) obtaining an activating composition of mesenchymal stem cells and/or macrophages activated by chemotherapy agent; and (b) administering the activating composition to a mammal in need of tissue regeneration, organ repair or reducing an inflammation.

In some embodiments of the invention, there is provided a method of initiating angiogenesis in a mammal, the method comprising:

(a) obtaining an activating composition of any cell type used for cell therapy that is activated by chemotherapy agent; and (b) administering the activating composition to a mammal in need of tissue regeneration or organ repair, wherein angiogenesis enhances tissue regeneration or organ repair.

In some embodiments of the invention, there is provided a method of initiating angiogenesis in a mammal, the method comprising:

(a) obtaining an activating composition of human mesenchymal stem cells and/or macrophages activated by a chemotherapy agent; and (b) administering the activating composition to a mammal in need of tissue regeneration or organ repair, wherein angiogenesis enhances tissue regeneration or organ repair.

In some embodiments of the invention, there is provided an activating composition comprising mesenchymal stem cells and/or macrophages and/or T cells and/or fibroblasts and/or neural tissue cells (such as astrocytes and glia cells) and/or adipose tissue-derived cells and/or other tissues resident cells that are activated by an anticancer drug.

The anticancer drug may be in some embodiments a chemotherapy agent.

In some embodiments of the invention, there is provided an activating composition comprising a conditioned medium from mesenchymal stem cells and/or macrophages and/or T cells and/or fibroblasts and/or neural tissue cells (such as astrocytes and glia cells) and/or adipose tissue-derived cells and/or other tissues' resident cells that were activated by an anticancer drug.

In some embodiments of the invention, there is provided a method for producing activated mesenchymal stem cells and/or activated macrophages and/or T cells and/or fibroblasts and/or neural tissue cells (such as astrocytes and glia cells) and/or adipose tissue-derived cells and/or other tissues' resident cells composition for use in tissue repair or for treating a disease associated with tissue damage, said method comprising: activating the mesenchymal stem cells and/or the macrophages and/or T cells and/or fibroblasts and/or neural tissue cells (such as astrocytes and glia cells) and/or adipose tissue-derived cells and/or other tissues resident cells by culturing the mesenchymal stem cells and/or the macrophages and/or T cells and/or fibroblasts and/or neural tissue cells (such as astrocytes and glia cells) and/or adipose tissue-derived cells and/or other tissues' resident cells with an anticancer drug and optionally separating a conditioned media from the activated mesenchymal stem cells and/or activated macrophages and/or T cells and/or fibroblasts, the activated mesenchymal stem cells and/or the macrophages and/or T cells and/or fibroblasts and/or neural tissue cells (such as astrocytes and glia cells) and/or adipose tissue-derived cells and/or other tissues' resident cells or the supernatant thereof are used in tissue repair or for treating the disease associated with tissue damage. In some embodiments of the invention, the step of culturing or incubating the cells with the anticancer agent lasts between about 10 minutes to about 72 hours.

In some embodiments of the invention, the conditioned media is collected from at least $10^5$-$10^7$ activated cells.

In some embodiments of the invention, there is provided a method for promoting tissue regeneration or organ repair of a damaged organ, and/or for reducing inflammation in a mammal, the method comprising: administering the activating composition of the invention to a mammal in need of tissue regeneration, organ repair or reducing an inflammation.

In some embodiments of the invention, there is provided a method of initiating angiogenesis and/or inducing immunosuppression in a mammal, the method comprising: administering the activating composition of the invention to a mammal in need of tissue regeneration or organ repair, wherein angiogenesis enhances tissue regeneration or organ repair of a damaged organ.

In some embodiments of the invention, there is provided a method of regenerating a tissue in a damaged organ comprising the steps of: applying the activated composition of the invention to the damaged organ either directly or by peripheral administration.

In some embodiments of the invention, the damaged organ is a pancreas, breast, ovary, lung, heart, kidney, lung, GI tract, intestine, skin, liver or brain.

In some embodiments of the invention, the anticancer drug is a chemotherapy agent selected from the group consisting of gemcitabine, paclitaxel, paclitaxel in combination with anakinra, anakinra, cisplatin, 5-FU, dacarbazine, temozolomide and any combination thereof or wherein the anticancer drug is an antibody, a molecularly targeted drug such as bortezomib, radiation, and immunotherapy agents including immune checkpoint inhibitors. In some embodiments of the invention wherein if:

the damaged organ is a pancreas and the chemotherapy agent is gemcitabine;

the damaged organ is a breast, ovaries or lung and the chemotherapy agent is paclitaxel;

the damaged organ is a heart and the chemotherapy agent is a combination of paclitaxel and anakinra;

the damaged organ is a kidney or lung and the chemotherapy agent is cisplatin;

the damaged organ is a GI tract or intestine and the chemotherapy agent is 5-FU;

the damaged organ is skin and the chemotherapy agent is dacarbazine;

the damaged organ is a brain and the chemotherapy agent is temozolomide; and the damages organ is a liver and the chemotherapy agent is gemcitabine In some embodiments of the invention, there is provided a method of treating or preventing a disease associated with tissue damage in a subject in need comprising the steps of applying the activated composition to the subject in need either directly to a degenerated organ or by peripheral administration.

In some embodiments of the invention, if the disease or the disorder is lung fibrosis the anticancer agent is paclitaxel, cisplatin or gemcitabine; if the disease or the disorder is liver fibrosis the anticancer agent is gemcitabine.

In some embodiments of the invention, there is provided a method of healing a wound comprising the step applying the activated composition of the invention to the wound.

In some embodiments of the invention, the anticancer drug is paclitaxel.

In some embodiments of the invention, the cell is incubated with the anticancer agent for between about 10 minutes to about 72 hours.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1 (A, B, and C): FIG. 1A: After 72 hours, the tumors were harvested, and tumor sections were immunostained using antibodies against CD105 (yellow) and aSMA (green) to identify MSCs, and CD133 (red) to identify CSCs. Nuclei were stained with DAPI (blue). Red arrows represent CSCs whereas white arrows represent MSCs. Scale bar, 100 μm.

FIGS. 2(A and B) show conditioned medium of gemcitabine-activated MSCs induce endothelial cell recruitment and promote immunosuppression Matrigel plugs containing 10% of conditioned medium (CM) generated from gemcitabine-activated MSCs or untreated MSCs were injected subcutaneously into the flanks of 8- to 10-week-old BALB/c mice. After 10 days, plugs were removed and stained for histology analysis and flow cytometry evaluation.

FIGS. 6(A, B, C and D) are graphs showing that chemo-activated stem cells inhibit lung tissue inflammation.

The cells, as in FIG. 5, were immunostained for different surface markers, evaluating immune cell lineage and their function such as an inflammatory or anti-inflammatory state. The cells were then analyzed by flow cytometry, and the percentage of cells in each sample were tested.

Figure 7:
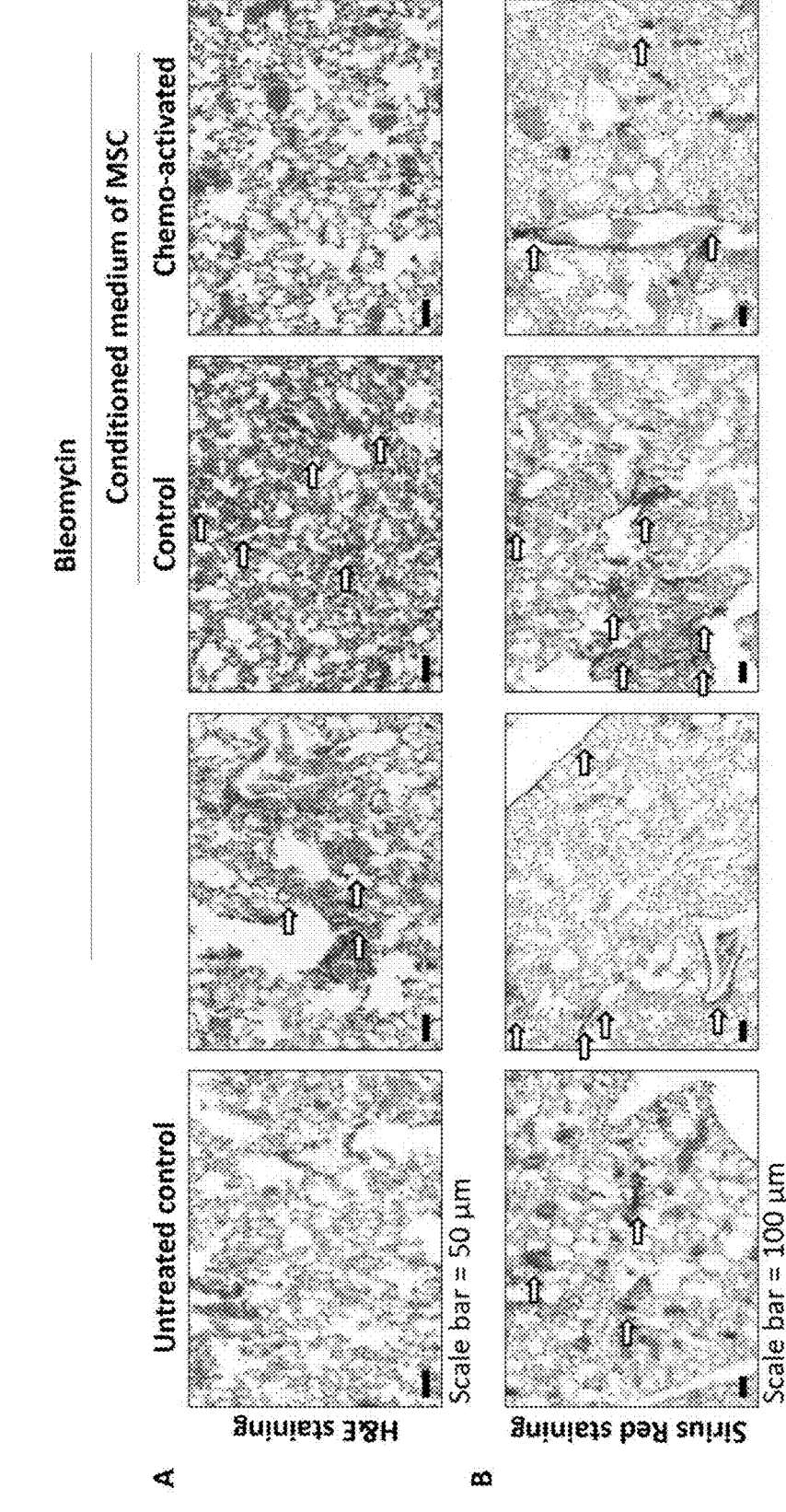
FIGS. 7(A and B) are photographs showing that chemo-activated mesenchymal stem cells reduce lung fibrosis.

Ten week old Balb/c mice were intratracheally (IT) administered with 0.04 units of Bleomycin (Baxter Oncology GmbH, Germany) or treated with vehicle control. After one week, mice were either left untreated or administered IT with conditioned medium (CM) of control-MSC or chemo-activated MSC. Treatment was given for a week, every other day. Fourteen days after Bleomycin administration, lungs were harvested and subsequently were fixated with PFA. Paraffin-embedded lung tissues were sectioned and stained with Hematoxylin and Eosin (H&E) solution (FIG. 7A) or Sirius Red to assess collagen content (FIG. 7B). The results demonstrated an extensive inflammatory process followed by increased collagen depositioning (represented by white arrows) in the lungs of belomycin-treated mice either control or MSC control administered mice whereas, in fibrotic lungs from mice administered with CM of chemo-activated MSCs, inflammation is completely abolished and collagen depositioning is reduced.

Figure 8:
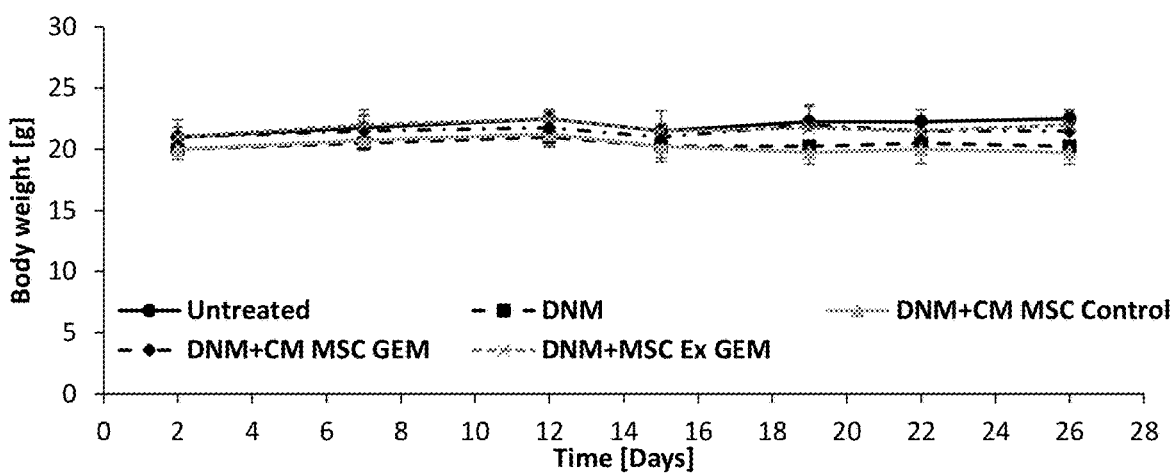

FIG. 8 is a graph showing that chemo-activated mesenchymal stem cell therapy did not induce toxicity, measured by total body weight.

Eight to ten-week-old female C57Bl/6 mice were administered intraperitoneally with DNM (5 mg/kg) or treated with vehicle control. Two weeks after treatment initiation, mice were either left untreated or injected with conditioned medium of control-MSC or chemo-activated-MSC or their exosomes fraction. The therapy was given every other day for a two-week period. Mice body weight was monitored every other day to reflect severe toxic effects of the therapy.

FIGS. 9(A, B and C) are graphs showing that chemo-activated MSC therapy restores liver physiology in the liver fibrosis model.

Eight to ten-week-old female C57Bl/6 mice were administered intraperitoneally with DNM (5 mg/kg) or treated with vehicle control. Two weeks after treatment initiation, mice were either left untreated or injected with conditioned medium of control-MSC or chemo-activated-MSC or their exosomes fraction. The therapy was given every other day for a two-week period. At the endpoint, blood was drawn from treated and control mice to assess liver physiological functions. The levels of albumin (FIG. 9A), alanine amino-transpherase (ALT, FIG. 9B), and aspartate aminotrans-pherase (AST, FIG. 9C) demonstrated that chemo-activated MSC therapy given ac conditioned medium or exosomes improved liver physiological parameters of the fibrotic livers.

FIGS. 10(A, B, C and D) are graphs showing that chemo-activated mesenchymal stem cells inhibit liver inflammation.

Single cell suspensions from the livers treated with DNM to generate fibrotic liver disease were immunostained for different surface markers evaluating fibroblasts and immune cell lineages. The cells were then analyzed by flow cytometry, and the percentage of cells in each sample was tested. Activated MSC therapy inhibited the percentage of pro-inflammatory cells (T helper cells, cytotoxic T cells (FIG. 10A), NK cells, B cells (FIG. 10B), MDSC, macrophages (FIG. 10C), fibroblasts and Kupffer cells (FIG. 10D)) and stimulated anti-inflammatory populations, including Kupffer cells and myeloid-derived suppressor cells (MDSC), thus suggesting that our therapy promotes an increased tissue regeneration of the liver.

FIGS. 11(A, B, C and D) show that chemo-activated mesenchymal stem cells reduce liver fibrosis.

Figure 11A:
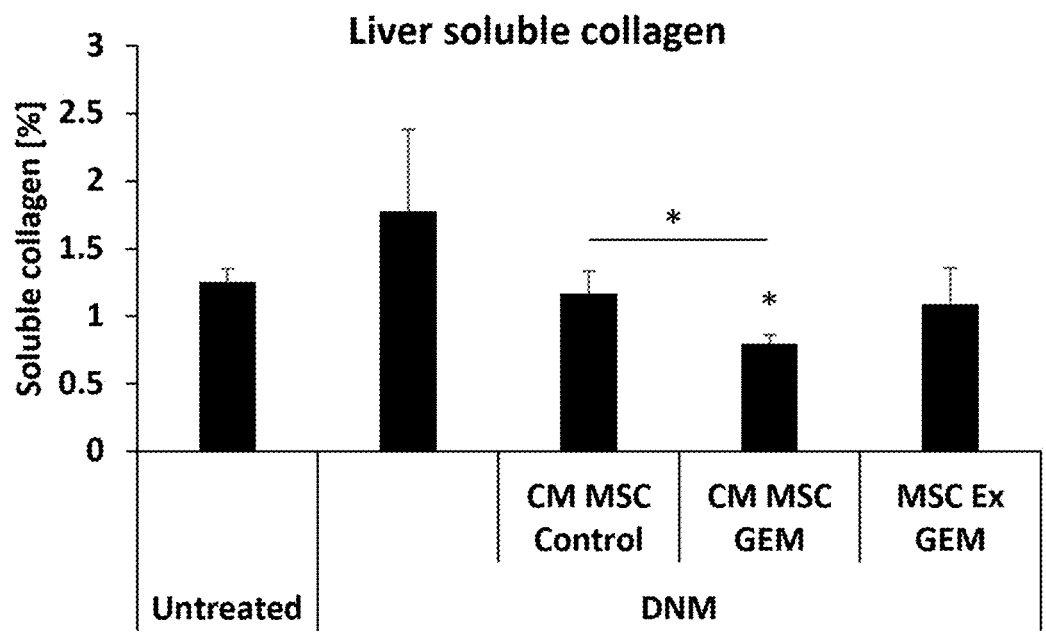
Figures 11B, 11C:
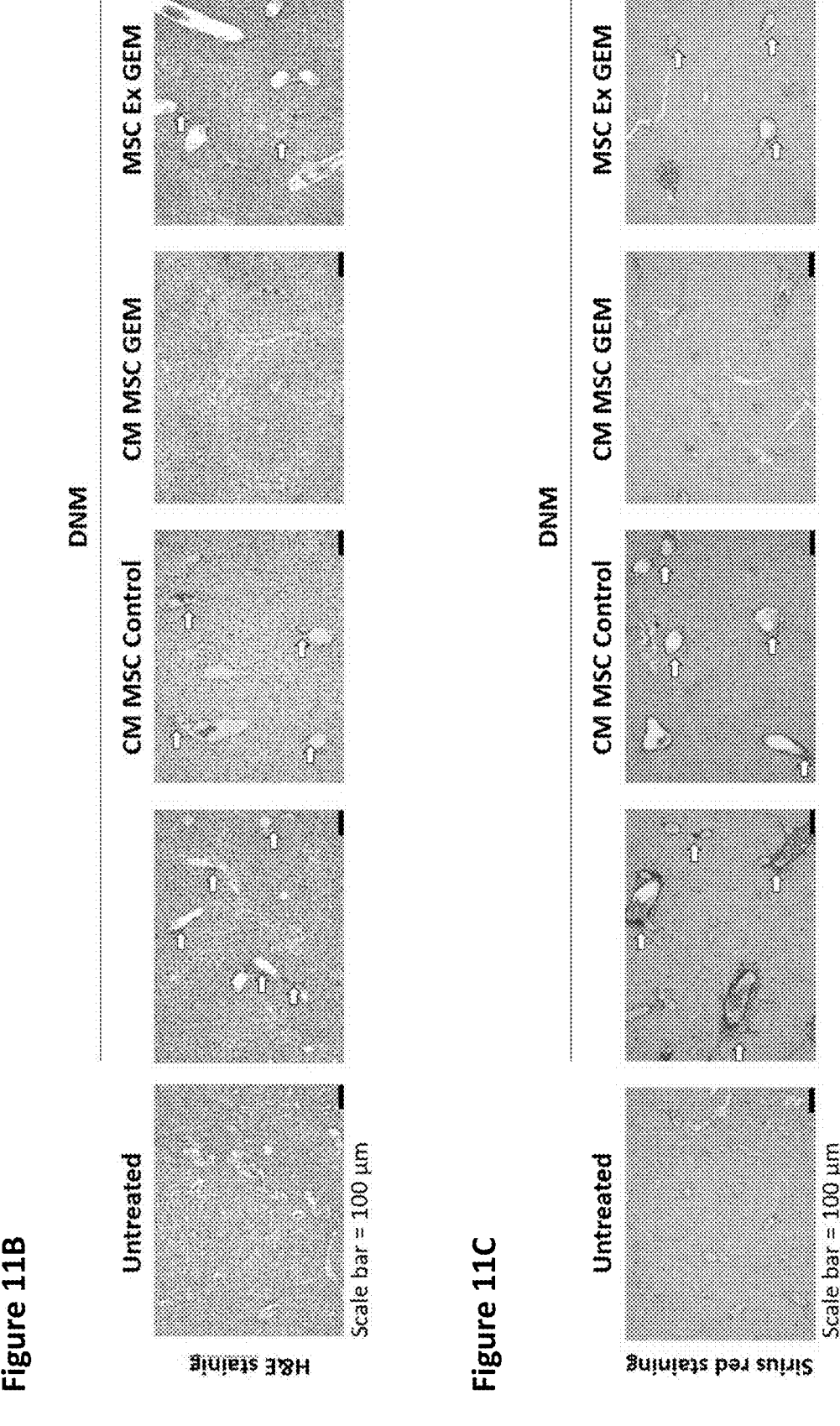
Figure 11D:
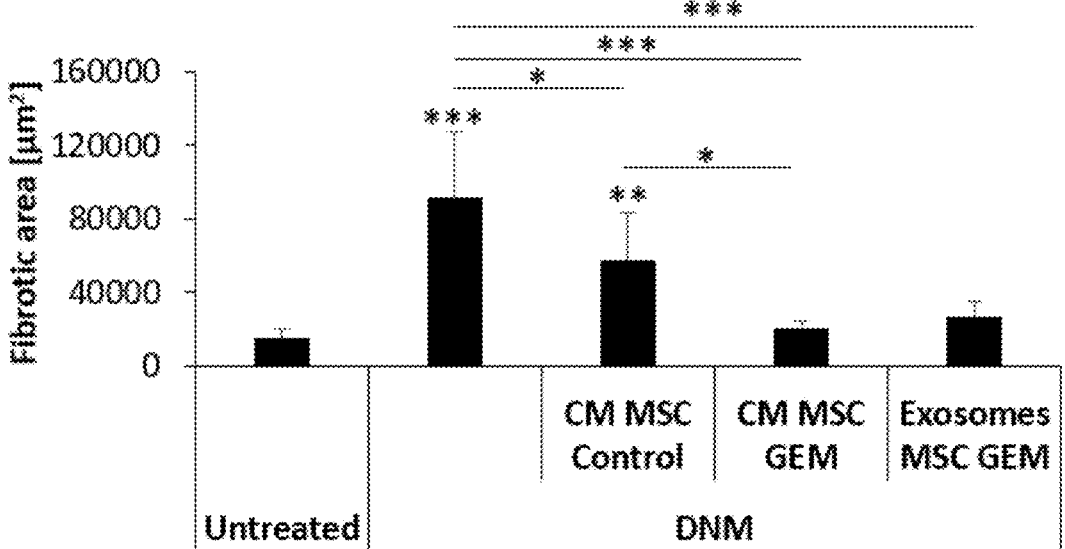

Eight to ten-week-old female C57Bl/6 mice were administered intraperitoneally with DNM (5 mg/kg) or treated with vehicle control. Two weeks after treatment initiation, mice were either left untreated or injected with conditioned medium of control-MSC or chemo-activated-MSC or their exosomes fraction. The therapy was given every other day for a two-week period. Four weeks after beginning of DNM treatment, mice were sacrificed, livers were harvested and processed for fibrosis assessment. Soluble collagen levels were substantially reduced in mice treated with CM of chemo-activated MSC when compared to other groups suggesting reduced liver fibrosis (FIG. 11A). In parallel, par-affin-embedded liver tissues were sectioned and stained with Hematoxylin and Eosin (H&E) solution (FIG. 11B) or Sirius Red to assess collagen content (FIG. 11C and FIG. 11D). The results demonstrated increased collagen depositioning (represented by white arrows) in the livers of DNM-treated mice, whereas in fibrotic livers from mice administered with CM of chemo-activated MSCs or their produced exosomes, collagen depositioning was reduced significantly to the levels of the untreated control.

DESCRIPTION OF THE DETAILED EMBODIMENTS OF THE INVENTION

Surprisingly, anticancer agents, such as, for example, chemotherapy agents, were found to be highly effective in activating mesenchymal stem cells (MSC), macrophages, fibroblasts, and T cells, both in vivo and in vitro, wherein the activated MSC, macrophages, fibroblasts, and T cells, or conditioned media thereof were found effective in regenerating tissues. More surprisingly, it was found that specific chemotherapy agents have explicit effects in a certain tissue and for specific clinical applications. Accordingly, the invention provides a method for the specific activation of various cells by a specific anticancer agent, such as a chemotherapy agent. The activated cells can be used for inducing tissue regeneration, repairing specific organs, and treating various conditions including lung or liver fibrosis. The present invention further provides a method for tissue repair including wound healing and fibrosis healing by locally treating the pathological or damaged tissue or organ with the activated products of mesenchymal stem cells and/or macro-phage and/or fibroblasts and/or any other cell type that may be used in cell therapy that were activated by an anticancer agent, such as a chemotherapy drug. Further provided is a method of treating a wound with a CM of mesenchymal stem cells and/or macrophage and/or fibroblasts and/or T-cells or any other cell type that may be used in cell therapy that were specifically activated by an anticancer agent, such as a chemotherapy agent.

In some embodiments of the invention, there is provided a method of treating or preventing a disease associated with tissue damage in a subject in need, the method comprising Contacting activated mesenchymal stem cells (MSC) and/or any other activated cells as described above and/or contacting a conditioned media of the activated MSC and/or any other activated cell with a tissue that underwent tissue damage in the subject in need, wherein the MSC are autologous or allogeneic non-transfected MSC.

As used herein, "preventing" or "prevention" or "inhibit" or "inhibition" interchangeably refers to the reduction of likelihood of the risk of acquiring a disease or disorder that may be a disease associated with tissue damage (for example, when the subject does not yet experience or display all symptoms of the disease, or the symptoms are minor, the outburst of the disease will be delayed or inhibited). Biological and physiological parameters for identifying such patients are well known to physicians and depend on the disease or disorder.

The terms "treatment" or "treating" of a subject includes the application or administration of the secreted cell products of activated MSC and/or other cells that can be used in the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required.

The term "tissue damage" refers herein to a pathological condition which include structural changes in extracellular matrix (ECM) or cells within a specific tissue, including burns, apoptotic cells or necrotic tissue. Such a damaged tissue may be due to immune or autoimmune activity, internal or external forces, inflammation process, trauma and the like.

In some embodiments of the invention, there is provided a method for treating or preventing a disease associated with tissue damage. The disease associated with tissue damage is one or more of the following diseases, conditions or disorders:

Osteoarthritis, avascular necrosis, or severe degenerative joint disease;

Stroke or degenerative brain disease selected from the group consisting of dementia, amyotrophic lateral sclerosis (ALS), Alzheimer's disease, Parkinson's disease, Huntington's disease, Pick's disease, Creutzfeldt-Jakob disease, and a combination thereof;

Muscular dystrophy such as, for example, Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies;

Fibrotic liver disease or liver degenerative disease, liver inflammatory conditions, cirrhosis;

Fibrotic lung disease, chronic obstruction pulmonary disease;

Autoimmune diseases such as lupus, type 1 diabetes, psoriasis, skin eczema;

Osteoarthritis, the most common form of arthritis, is a disease characterized by slow degenerative processes in the articular cartilage, subchondral bone associated with marginal osteophyte formation, and low grade inflammation. Osteoarthritis is believed to affect 15% of the population in its chronic form. Of those, one-quarter are severely disabled. Most cases of osteoarthritis have no known cause and are referred to as primary osteoarthritis. When the cause of the osteoarthritis is known, the condition is referred to as secondary osteoarthritis. Secondary osteoarthritis is caused by another disease or condition. Conditions that can lead to secondary osteoarthritis include repeated trauma or surgery to the joint structures, abnormal joints at birth (congenital abnormalities), gout, diabetes, and other hormone disorders. Other forms of arthritis are systemic illnesses, such as rheumatoid arthritis and systemic lupus erythematosus (SLE);

Osteoarthritis involves mainly the hips, knees, spine, and the interphalangeal joints. In severe osteoarthritis, complete loss of cartilage cushion causes friction between bones, causing pain at rest or pain with limited motion. Osteoarthritis is characterized by a slow degradation of cartilage over several years;

Retinal degenerative disorder, Refsum disease, Smith-Lemli-Opitz syndrome, Schnyder crystalline corneal dystrophy, drusen, age-related macular degeneration, and diabetic retinopathy;

Some other examples: Alzheimer's disease (AD), Amyotrophic lateral sclerosis (ALS, Lou Gehrig's Disease), Charcot-Marie-Tooth disease (CMT), Chronic traumatic encephalopathy, Cystic fibrosis, Some cytochrome c oxidase deficiencies (often the cause of degenerative Leigh syndrome), Ehlers-Danlos syndrome, Fibrodysplasia ossificans progressiva, Friedreich's ataxia, Frontotemporal dementia (FTD), cardiovascular diseases (e.g. atherosclerotic ones like coronary artery disease, aortic stenosis etc.), Huntington's disease, Infantile neuroaxonal dystrophy, Keratoconus (KC), Keratoglobus, Leukodystrophies, Macular degeneration (AMD), Marfan's syndrome (MFS), Some mitochondrial myopathies, Mitochondrial DNA depletion syndrome, Multiple sclerosis (MS), Multiple system atrophy, Muscular dystrophies (MD), Neuronal ceroid lipofuscinosis, Niemann-Pick diseases, Osteoarthritis, Osteoporosis, Parkinson's disease, Pulmonary arterial hypertension, prion diseases (Creutzfeldt-Jakob disease, fatal familial insomnia etc.), Progressive supranuclear palsy, Retinitis pigmentosa (RP), Rheumatoid arthritis, Sandhoff Disease, Spinal muscular atrophy (SMA, motor neuron disease), Subacute sclerosing panencephalitis, Tay-Sachs disease, Vascular dementia (might not itself be neurodegenerative, but appears often alongside with other forms of degenerative dementia);

Other examples are burns, bone raptures, wounds, diabetic wounds such as in diabetes type 1;

Further examples are autoimmune diseases, such as, for example, rheumatic arthritis, psoriasis, sarcoidosis, celiac disease, diabetes mellitus type 1, Graves' disease, inflammatory bowel disease, multiple sclerosis, psoriasis, rheumatoid arthritis, and systemic lupus erythematosus;

"Activated cells" or "activated mesenchymal stem cells" or "activated macrophage cells" or "activated fibroblast cells" etc. refer herein to cells, mesenchymal stem cells or macrophages or other cells that were previously educated with an anticancer agent for a period of at least 10, 20, 30, 40, 50 minutes or an hour, 2, 3, 4, 5, 6, 7, 8, 9, 10, 12, 14, 16, 18, 20, 22 24, 48 or 72 hours or more using standard serum-free medium. It is noted that the incubation should be terminated before the cells undergo apoptosis and/or death. These activated cells or the conditioned media therefrom may be used in the methods described herein. Examples for such an anticancer agent is Gemcitabine, Paclitaxel, Paclitaxel and Anakinra, Cisplatin, 5-FU, Dacarbazine, Temozolomide targeted drugs (e.g. Bortezomib), radiation, antiangiogenic drugs and immune checkpoint inhibitors antibodies. The term "activating composition" includes either cells that are activated by an anticancer therapy or the conditioned media thereof, or both. The conditioned media may be diluted, or concentrated or lyophilized. The activated cells are any of the following: activated mesenchymal stem cells and/or activated macrophages and/or T cells and/or fibroblasts and/or neural tissue cells (such as astrocytes and glia cells) and/or adipose tissue-derived cells and/or other tissues resident cells or any other activated cell that can be used in tissue repair.

The number of the activated MSC or the any other activated cell of the invention, or the conditioned medium produced therefrom, the administration dosage form and the dosing regimen as well as the location in case of a local administration depend on the type of the disease or the disorder, the location of the damaged tissue or organ and the severity of the disease. In most cases, but not exclusively, the conditioned medium was produced from at least $10^5$-$10^6$ cells per 1 ml. In some embodiments, the treatment is by using at least between 1-10×$10^6$ cells, per treatment.

It should be noted that in some embodiments of the invention, the conditioned medium can be concentrated by centrifugation at, for example, 1100,000 g to obtain exosomes and other products. In some cases, the conditioned medium can be lyophilized in order to keep it as dry product for a later use in reconstitution, for example. It is noted that the in the method of treatment of the invention, the term "conditioned medium" or "conditioned media" or "CM" refers also to the secretome, the dry product, the supernatant, as well as to untouched conditioned media.

For example, for a method of treating disc degeneration in a patient, the method comprising: injecting activated mesenchymal stem cells (MSC) or conditioned media of the activated MSC directly into a lumbar associated muscle proximal to a lumbar disc of the patient, wherein the MSC are autologous or allogeneic non-transfected MSC; wherein the lumbar associated muscle is selected from the group consisting of psoas major muscle, multifidus muscle, transversospinalis muscle and sacrospinalis muscle. The treatment dosing regimen is from 1-10 times, the number of the cells is $1\times10^6$ cells after the cells were activated. In some cases, activated cell conditioned medium as specified above can be injected in a volume of 100 µl for 1-10 times or more based on healing process monitoring.

Chemotherapy-Activated MSCs Enrich for Stem Cells

Figure 1A:
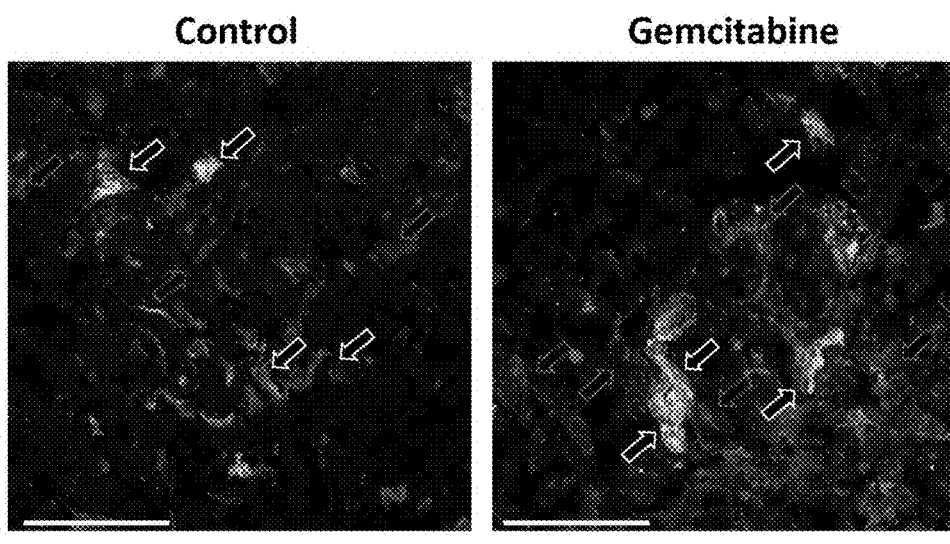
FIG. 1A is a photograph showing that Gemcitabine promotes MSCs homing to tumors and induces enrichment of stem cells populations Eight-to-ten-week-old SCID mice were subcutaneously implanted with PANC1 cells (n=5 mice/group). When tumors reached 500 mm$^3$, mice were treated with gemcitabine (500 mg/kg) or vehicle control.
Figure 1B:
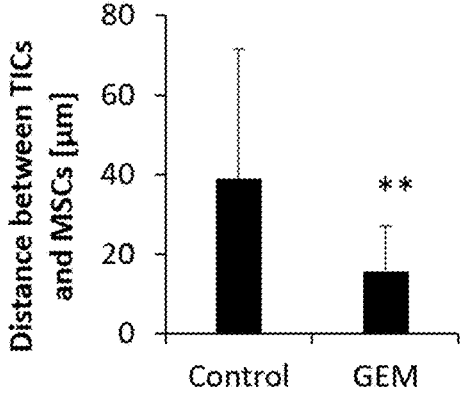
FIG. 1B: Right Left side is a graph showing the distance between MSCs and CSCs as was measured and plotted (n>15 fields/group) and FIG. 1B left-right side is a graph showing the percentage of MSCs in tumor single cell suspensions was quantified by flow cytometry.
Figure 1B:
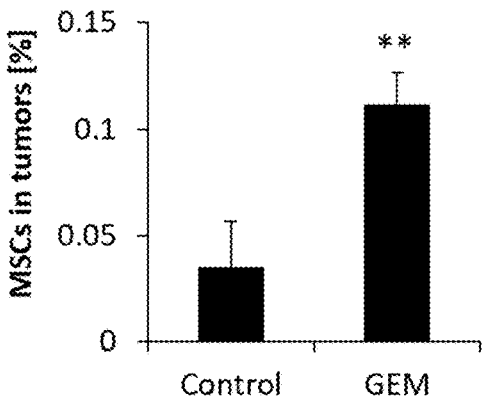
Figure 1C:
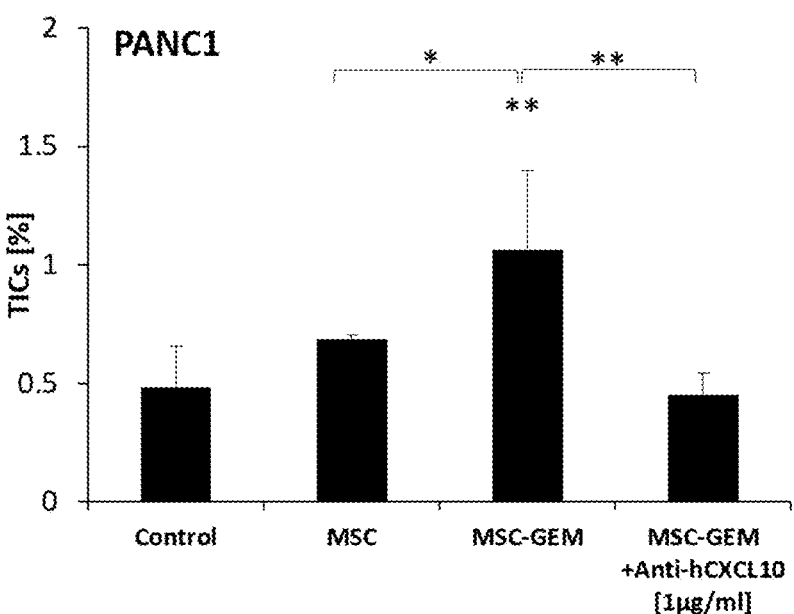
FIG. 1C: A graph showing the percentage of TICs in culture as was assessed by a flow cytometry: PANC1 cells were cultured in serum-free medium (control) or serum-free medium supplemented with conditioned medium derived from cultures of control MSCs (MSC), gemcitabine-educated MSCs (MSC-GEM) or gemcitabine- and anti-CXCL10-treated MSCs (MSC-GEM+anti-hCXCL10). After 3 days, the percentage of TICs in culture was assessed by flow cytometry.

MSCs are one of the major candidates for tissue regeneration and cell therapy due to their high proliferative potential and ability to differentiate to main mesenchymal tissues. Moreover, MSCs have been shown to contribute to systemic resistance to chemotherapy in solid tumors by the secretion of two specific fatty acids following exposure to platinum-based cytotoxic agents. These fatty acids indirectly protect colon and lung carcinoma cells from the cytotoxic effects of the chemotherapy. However, the interactions of MSCs with tissue-resident stem cells are not yet clear, especially following chemotherapy. To this end, as can be seen in the Examples, subcutaneous pancreatic tumors were analyzed, generated by injection of PANC1 cells to flanks of 8- to 10-week-old SCID mice. When tumors reached a certain size, mice were treated with gemcitabine and after three days mice were removed and sacrificed. Immunostaining of the tumors for MSCs and cancer stem cells (CSCs), a rare population of tumor cells with increased resistance capacity and increased tumorigenicity was demonstrated following gemcitabine therapy. Specifically, MSCs home to tumors and locate in close proximity to CSCs, when compared to untreated control (FIG. 1A). In addition, FIG. 1B demonstrates that chemotherapy induced massive recruitment of MSCs to pancreatic tumors, which is similar to MSC infiltration to damaged tissue sites. Furthermore, to study, whether MSCs contribute to CSC repopulation, conditioned media (CM) of untreated MSCs or gemcitabine-educated MSCs was applied and CSC enrichment was evaluated using phenotypic characterization by flow cytometry. Activation of MSCs with chemotherapy resulted in significant enrichment of CSCs when compared to the effect of untreated MSCs. Secretome analysis of gemcitabine-activated MSCs revealed that CXCL10, among many other factors which affect tissue remodeling and/or regeneration, is highly elevated in the conditioned medium following chemotherapy treatment, relative to untreated MSCs, as presented in Table 2. CXCL10 was shown to promote CSC enrichment by binding to CXCR3 receptor and consecutive induction of STAT3 signaling. CXCL10 neutralization with anti-CXCL10 antibody, canceled the enrichment effect of chemotherapy-activated MSCs on CSC (FIG. 1C).

Chemotherapy-Activated MSCs Promote Immunosuppression and Induce Angiogenesis

Figure 2A:
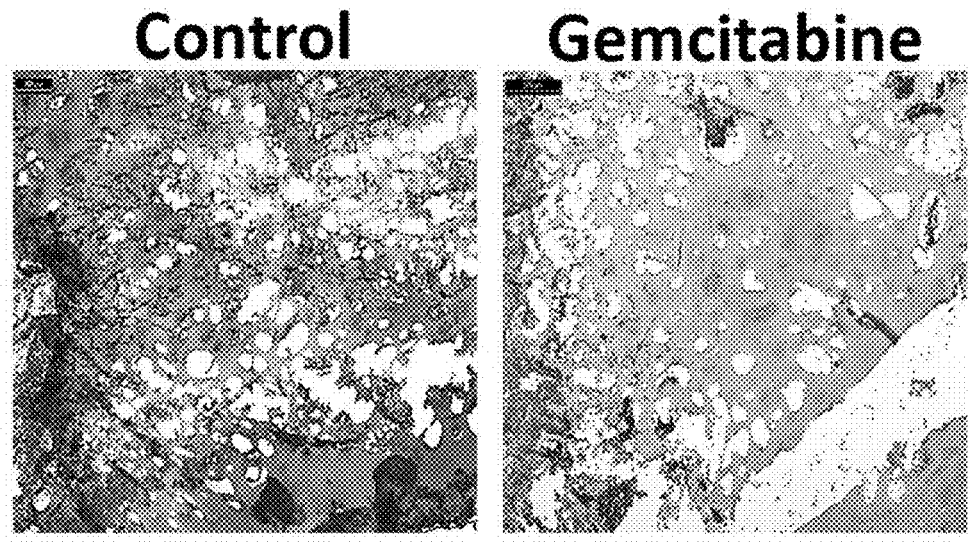
FIG. 2A shows Hematoxylin & Eosin staining of Matrigel plugs, containing CM from control (left side) or gemcitabine-activated MSCs (right side).
Figure 2B:
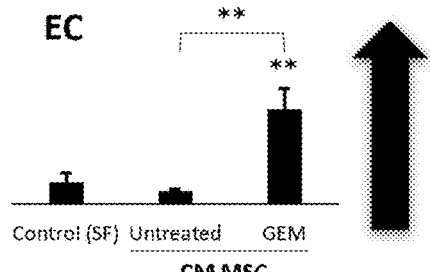
FIG. 2B presents Matrigel plugs which were processed as single cell suspensions, were immunostained for different cell types and analyzed by flow cytometry as indicated in the figure.
Figure 2B:
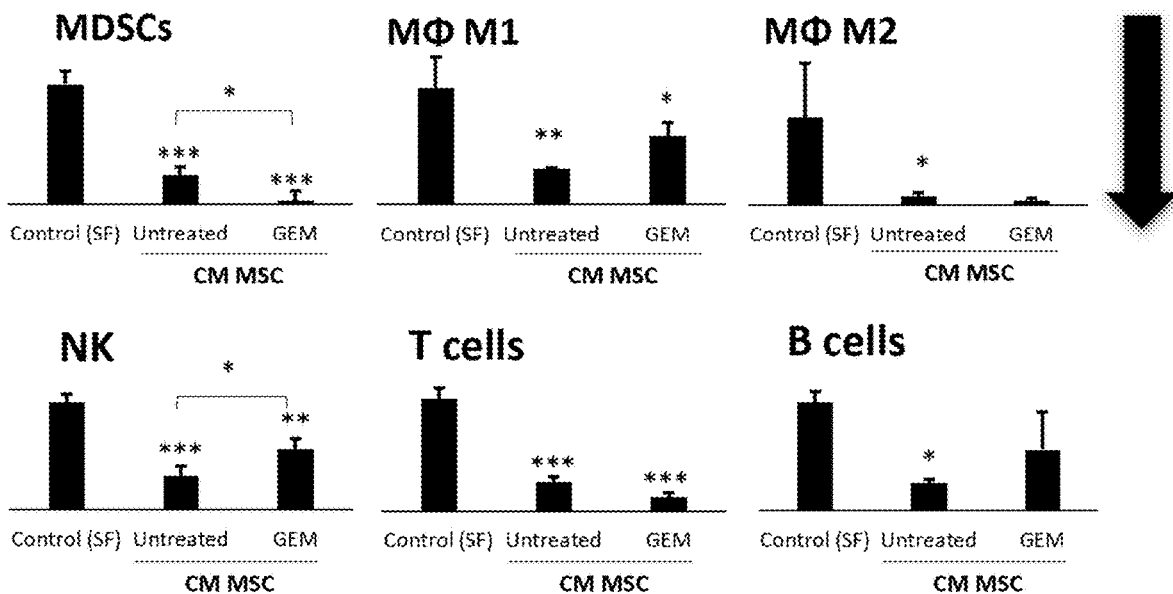
Figure 3A:
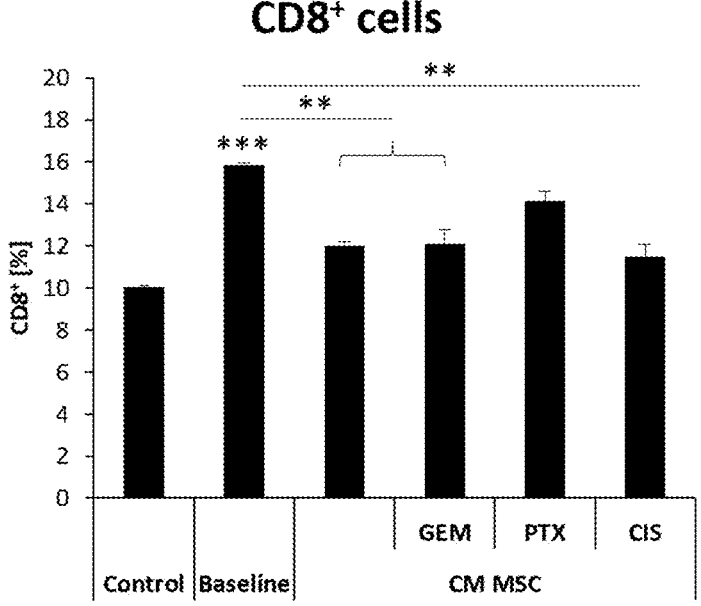
FIGS. 3(A, B and C) are graphs showing that chemotherapy-activated MSCs inhibit T cell activation Splenocytes isolated from naïve 8-10-week-old BALB/c mice were cultured with CD3$^+$/CD28$^+$ T cell activating beads in the absence (baseline) or presence of the CM of untreated MSCs or chemotherapy-activated MSCs. Twenty-four hours later, the splenocytes were harvested and the percentage of activated cytotoxic T cells (CD8$^+$ (FIG. 3A), CD8$^+$/CD25$^+$ (FIG. 3B) or CD8$^+$/CD107a$^+$ FIG. 3C) was evaluated by flow cytometry. NC—Negative control (splenocytes cultured in the absence of activation beads), GEM—gemcitabine, PTX—paclitaxel, CIS—cisplatin.
Figure 3B:
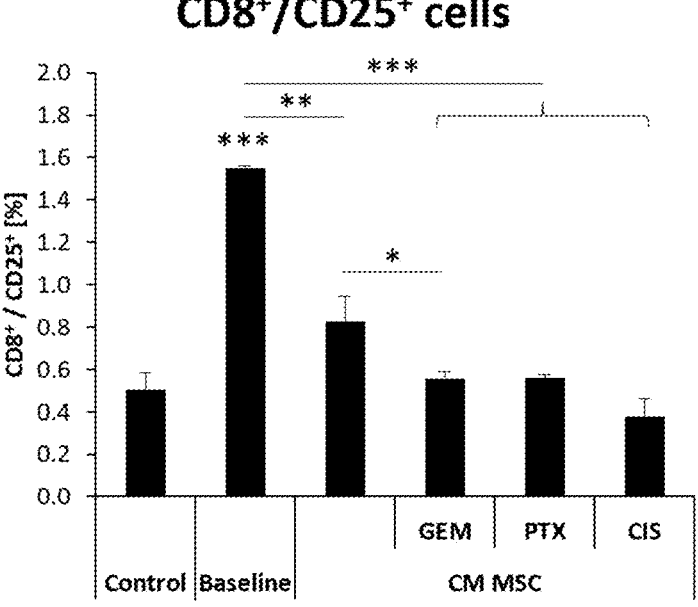
Figure 3C:
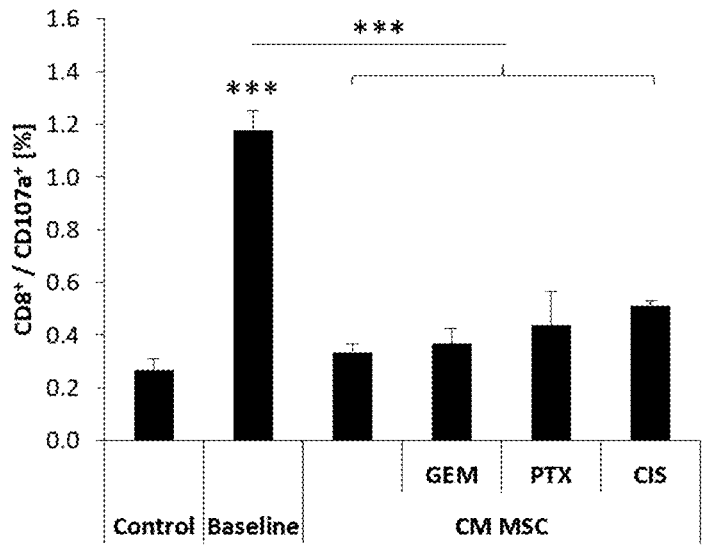

MSCs are known for their ability to home to injured sites and promote tissue regeneration. Moreover, MSCs secrete a whole milieu of cytokines and chemokines including TGFβ, IL-6, PGE$_2$, IDO, LIF to modulate recruitment of various hematopoietic cell types which modulate tissue structure. Matrigel plug assay was conducted to test these abilities. To this end, Matrigel plugs which contained conditioned medium (CM) generated from untreated or gemcitabine-educated MSCs were implanted into the flanks of Balb/c mice. After 10 days, plugs were removed and prepared as single cell suspension. The cells from the plugs were phenotypically analyzed by flow cytometry to identify cells that were recruited to the plugs. It was shown that CM from gemcitabine treated MSCs induced the recruitment of endothelial cells, suggesting an increased angiogenic potential following gemcitabine therapy. In addition, the colonization of most immune populations, including macrophages, NK cells, T cells and B cells was significantly decreased in Matrigel plugs with CM from gemcitabine-activated MSC when compared to plugs containing CM of control MSCs (FIG. 2A-B). To further elaborate the immunomodulatory effects of chemotherapy-exposed MSCs, T cell activation assay was performed by applying the CM of naïve or chemotherapy-activated MSC on splenocytes extracted from naïve Balb/c mice. As a result, chemotherapy-activated MSC significantly decreased the total amount of CD8 T cells and suppressed the activation of cytotoxic T cells (FIG. 3). Overall, the results provided an additional support that in tumors, similar to damaged tissue, MSC obtain strong regenerative abilities facilitated by increased angiogenesis and an induction of immunosuppression in order to increase overall tissue repair.

Chemotherapy Activated MSCs Increase Effective Tissue Repair

Figure 4A:
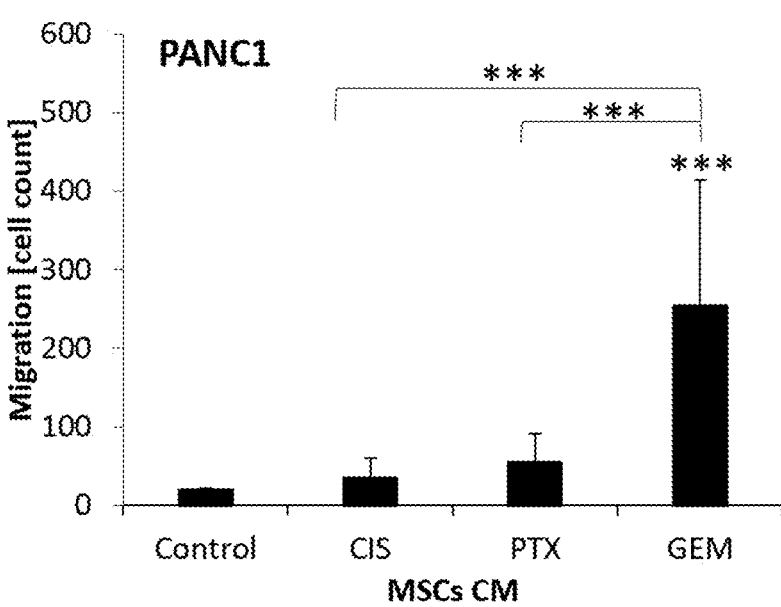
FIGS. 4(A, B, C and D) show that chemotherapy-activated MSCs induce wound healing PANC1 (2×10$^5$ cells) were evaluated for their migration properties using the Boyden chamber assay. The cells were tested in the presence of CM obtained from MSCs exposed to several types of chemotherapy drugs as indicated in the graph in FIG. 4A. PANC1 cells were analyzed for their motility properties using the scratch wound assay, when they were cultured in the presence of CM from control or chemotherapy-activated MSC as shown in FIGS. 4B and 4C. In vivo evaluation of wound healing properties in mice injected with chemotherapy-activated MSCs or their controls is demonstrated in the photograph of FIG. 4D. Briefly, small incisions were performed on the back of 8- to 10-week-old BALB/c mice. On the next day, the wounds were externally treated with the conditioned medium of control MSCs or gemcitabine-educated MSCs. The therapy was performed every other day until the end of the experiment. The healing process was tracked every other day for the period of two weeks until the complete closure of the wound was achieved.
Figure 4B:
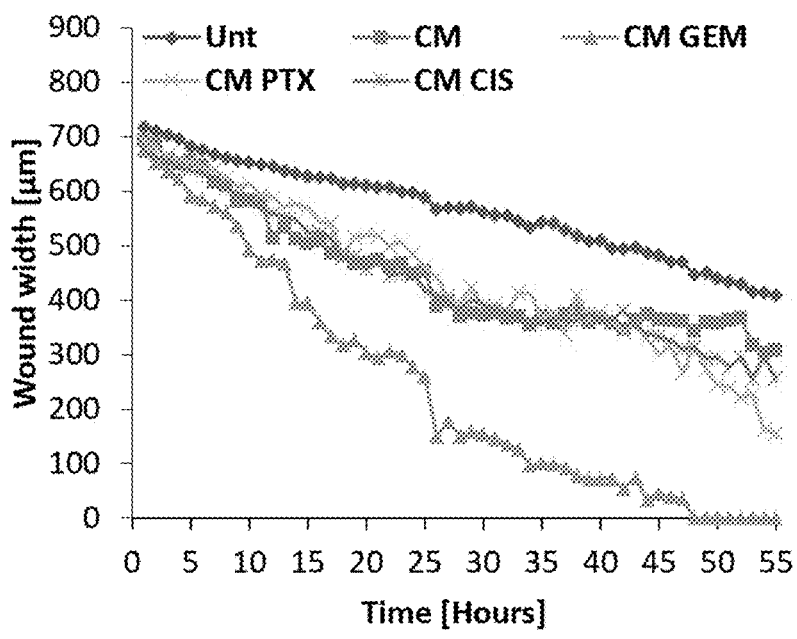
Figure 4C:
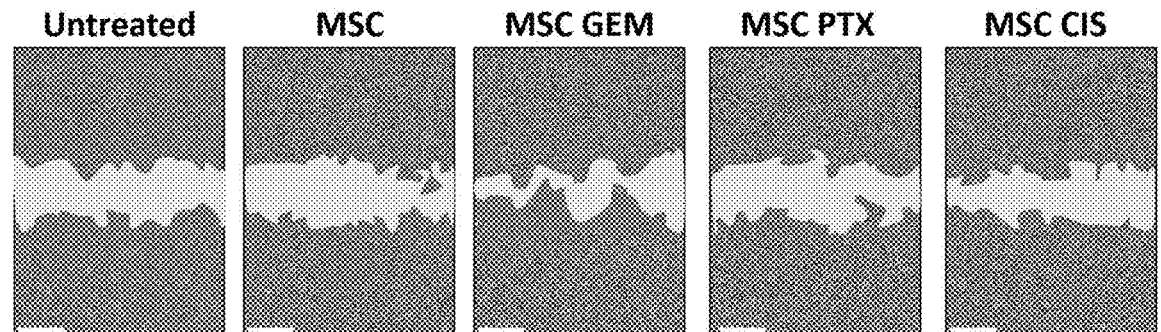

Based on the enhanced proangiogenic and immunosuppressive properties of chemotherapy-activated MSCs, the ability of MSC to heal wounds was tested. To this end, the effect of MSCs on the migratory properties of other cells was tested by performing a Modified Boyden chamber assay, as described in Material and Methods. To do so, PANC1 were cultured in the upper chamber of the well, whereas the lower chamber was loaded with the CM of chemotherapy-activated MSCs or CM of untreated MSCs. After 24 hours, the cells that migrated to the lower side of the chamber, were fixed and subsequently stained with crystal violet. It was found that CM of gemcitabine-activated MSCs dramatically increased the migration properties of PANC1 cells, compared to control group. Interestingly, CM generated from MSCs exposed to other cytotoxic agents such as paclitaxel and cisplatin did not affect migration abilities of the cells (FIG. 4A). In addition, scratch wound assay was generated to further demonstrate the regenerative potential of chemotherapy-activated MSCs. Cells treated with the CM of gemcitabine-educated MSC closed the gap faster than untreated control cells or cells exposed to CM of untreated MSCs (FIGS. 4B and 4C). In parallel with the migration assay results, wound closure time of cells treated with CM from MSC exposed to PTX or cisplatin was similar to the control groups.

Figure 4D:
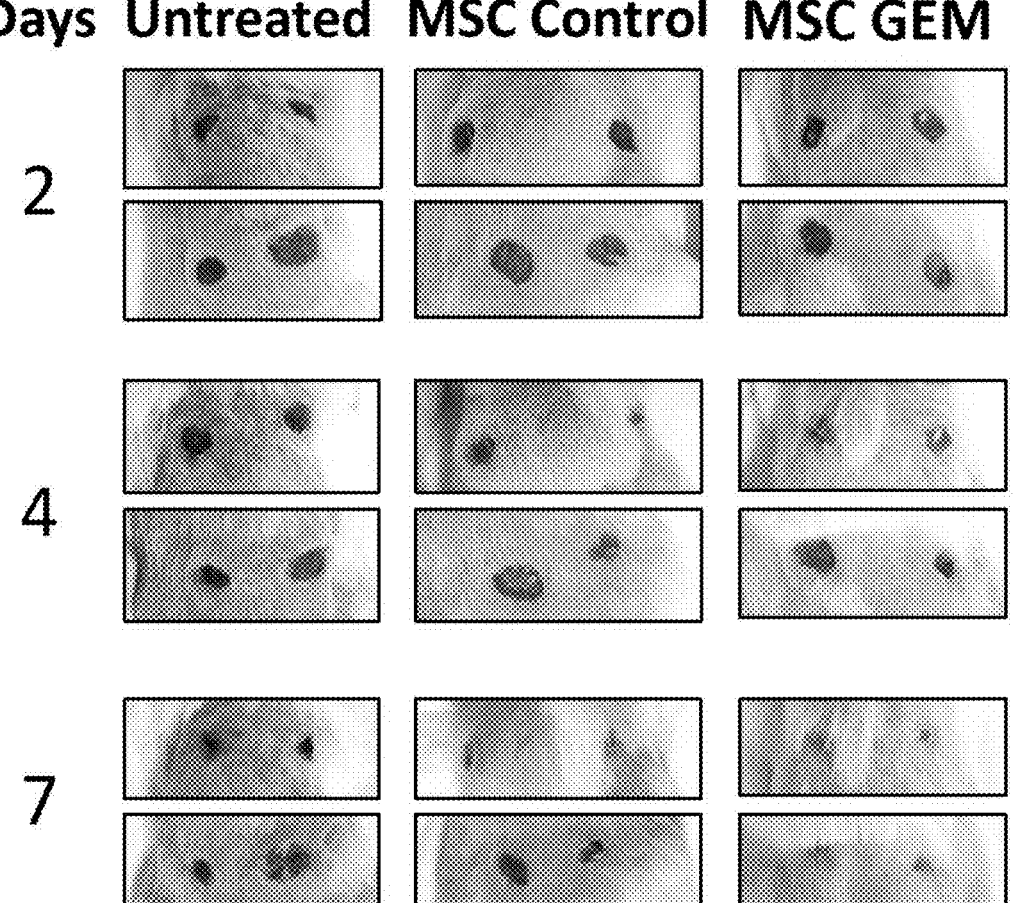

Next, the wound healing properties of chemotherapy-activated MSCs was tested in vivo. For this purpose, 0.5 cm incisions were performed on the back of SCID mice. After 24 hours, the wounds were externally treated with the conditioned medium of control MSCs or MSC pre-exposed to 10 nM gemcitabine. Control mice were left untreated. Wound healing was monitored until the complete closure of the wound. The results showed that wound healing in mice treated with gemcitabine-activated MSCs was the fastest comparing to control groups (FIG. 4D). Taken together, our results demonstrate that chemotherapy-educated MSC drastically induces MSCs regenerative and wound healing characteristics, therefore contributing to damage repair.

In an embodiment of the invention it was shown that a chemotherapy agent may be used for activating cells, such as macrophages and/or MSCs, and/or T cells and/or fibroblasts that can be used for various indications in which cell regeneration is required. Some examples are demonstrated in Table 1 below. In some embodiments, the therapeutic effect of a specific chemotherapy agent, reflected, for example, in cell regeneration, is specific to a certain organ, as exemplified in Table 1.

In an embodiment of the invention, there is provided an activating composition, as hereinafter defined. According to some embodiments of the invention the activating composition comprises mesenchymal stem cells and/or macrophages and/or T cells and/or fibroblasts that were activated by an anticancer agent, such as a chemotherapy agent. In other embodiments, the activating composition comprises the supernatant or the conditioned media of a preparation that includes a mesenchymal stem cells and/or macrophages and/or T cells and/or fibroblasts that were activated by a specific anticancer agent such as a chemotherapy agent and that was separated, for example, by centrifugation, using the secretome of such activated cells. The term "secretome" refers to proteins, metabolites, enzymes, lipids, sugar molecules, and extracellular vesicles, such as exosomes that are secreted by cells into the extracellular space.

"extracellular vesicles" "exosomes" are blubbing or secretion of small vesicles from cells which contains proteins, RNA, DNA and other biological materials which can be transferred between cells. These vesicles have been shown to act in physiological and pathological conditions.

In some embodiments of the invention, there is provided an activating composition comprising mesenchymal stem cells and/or macrophages that is activated by a chemotherapy agent, wherein the mesenchymal stem cells and/or macrophages and/or T cells and/or fibroblasts that are activated by a chemotherapy agent are separated from the conditioned medium and wherein the conditioned medium is used as a therapy.

In some embodiments of the invention, there is provided a method to produce activated mesenchymal stem cells and/or activated macrophages and/or T cells and/or fibroblasts and/or neural tissue cells (such as astrocytes and glia cells) and/or adipose tissue-derived cells and/or other tissues resident cells for use in tissue repair comprising: activating the mesenchymal stem cell and/or the macrophages and/or T cells and/or fibroblasts and/or neural tissue cells (such as astrocytes and glia cells) and/or adipose tissue-derived cells and/or other tissues resident cells by culturing the mesenchymal stem cells and/or the macrophages and/or T cells and/or fibroblasts and/or neural tissue cells (such as astrocytes and glia cells) and/or adipose tissue-derived cells and/or other tissues resident cells with an appropriate chemotherapy agent.

In some embodiments of the invention there is provided a method for promoting tissue regeneration, organ repair or for reducing inflammation in a mammal, the method comprising:
(a) obtaining an activating composition of mesenchymal stem cells and/or macrophages and/or T cells and/or fibroblasts and/or neural tissue cells (such as astrocytes and glia cells) and/or adipose tissue-derived cells and/or other tissues resident cells activated by a chemotherapy agent; and
(b) administering the activating composition to a mammal in need of tissue regeneration, organ repair or reducing inflammation.

In some embodiments of the invention there is provided a method of initiating angiogenesis in a mammal, the method comprising:
(a) obtaining an activating composition of human mesenchymal stem cells and/or macrophages and/or T cells and/or fibroblasts and/or adipose tissue-derived cells and/or other tissues' resident cells activated by a chemotherapy agent; and (b) administering the activating composition to a mammal in need of tissue regeneration or organ repair, wherein angiogenesis enhances tissue regeneration or organ repair.

In an embodiment of the invention, there is provided a method of regenerating a tissue in a damaged organ comprising the steps of contacting macrophages and/or mesenchymal stem cells and/or T cells and/or fibroblasts and/or neural tissue cells (such as astrocytes and glia cells) and/or adipose tissue-derived cells and/or other tissues' resident cells with a chemotherapy agent, so as to provide activated macrophages and/or activated mesenchymal stem cells and/or T cells and/or fibroblasts and/or neural tissue cells (such as astrocytes and glia cells) and/or adipose tissue-derived cells and/or other tissues resident cells, and applying the activated cells to the damaged organ.

In some embodiments of the invention, the damaged organ is a pancreas, breast, ovary, lung, heart, kidney, lung, GI tract, intestine, skin, liver or brain. In some embodiments, the chemotherapy agent is gemcitabine, paclitaxel, paclitaxel in combination with anakinra, anakinra, cisplatin, 5-FU, dacarbazine or temozolomide, or any combination thereof.

In some embodiments of the invention, if the damaged organ is a pancreas, the chemotherapy agent that is used for cell activation is gemcitabine.

In some embodiments of the invention, if the damaged organ is a breast, ovary or lung, the chemotherapy agent that is used for cell activation is paclitaxel.

In some embodiments of the invention, if the damaged organ is a heart, the chemotherapy agent that is used for cell activation is a combination of paclitaxel and anakinra or anakinra alone.

In some embodiments of the invention, if the damaged organ is a kidney, ovary or lung, the chemotherapy agent that is used for cell activation is cisplatin.

In some embodiments of the invention, if the damaged organ is the GI tract, e.g., the intestine, the chemotherapy agent that is used for cell activation is 5-FU.

In some embodiments of the invention, if the damaged organ is skin, the chemotherapy agent that is used for activation is dacarbazine.

In some embodiments of the invention, if the damaged organ is the brain, the chemotherapy agent that is used for activation is temozolomide.

In some embodiments of the invention, there is provided a method of treating pancreatitis comprising the steps of contacting mesenchymal stem cells, and/or macrophages and/or T cells and/or fibroblasts and/or adipose tissue-derived cells and/or other tissues resident cells and/or any other cell type used for cell therapy with a chemotherapy agent so as to provide activated mesenchymal stem cells, macrophages and/or T cells and/or fibroblasts and/or adipose tissue-derived cells and/or other tissues resident cells and/or any other cell type used for cell therapy, and applying the activated mesenchymal stem cells, macrophages and/or T cells and/or fibroblasts and/or adipose tissue-derived cells and/or other tissues resident cells and/or the cell type used for cell therapy that is activated to the pancreas either by direct injection or by peripheral administration. In some embodiments the chemotherapy agent is gemcitabine. In some embodiments, an activating composition that comprises mesenchymal stem cells and/or macrophages and/or T cells and/or fibroblasts and/or adipose tissue-derived cells and/or other tissues' resident cells and/or any other cell type that can be used in cell therapy that are activated by a chemotherapy agent, wherein the mesenchymal stem cells and/or the macrophages and/or T cells and/or fibroblasts and/or adipose tissue-derived cells and/or other tissue resident cells and/or other cell type that is used in cell therapy that are activated by a specific chemotherapy agent were separated from a supernatant and wherein the supernatant is used as a therapy can be used in the method of treating described above.

In some embodiments of the invention, there is provided a method of treating a breast, lung or ovary injury comprising the steps of contacting macrophages or mesenchymal stem cells and/or T cells and/or fibroblasts and/or adipose tissue-derived cells and/or other tissues' resident cells or any other cell type used for cell therapy with a chemotherapy agent, so as to provide activated macrophages and/or activated mesenchymal stem cells, or and/or T cells and/or fibroblasts and/or adipose tissue-derived cells and/or other tissues resident cells and/or other activated cell type used for cell therapy and applying the activated macrophages and/or the activated mesenchymal stem cells and/or T cells and/or fibroblasts and/or adipose tissue-derived cells and/or other tissues resident cells or the activated cell type used for cell therapy to the breast, lung or ovary. In some embodiments the chemotherapy agent is paclitaxel.

In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues resident cells and/or any other cell type that can be used in cell therapy that are activated by a chemotherapy agent, wherein the mesenchymal stem cells and/or the macrophages and/or T cells and/or fibroblasts and/or neural tissue cells (such as astrocytes and glia cells) and/or adipose tissue-derived cells and/or other tissues resident cells and/or other cell type that is used in cell therapy that are activated by a specific chemotherapy agent were separated from a supernatant and wherein the supernatant is used as a therapy can be used in the method of treating described above.

In some embodiments of the invention, there is provided a method of treating myocardial infarction (MI) or heart failure comprising the steps of contacting macrophages or mesenchymal stem cells and/or any other cell type used for cell therapy with a chemotherapy agent so as to provide activated macrophages or activated mesenchymal stem cells and/or T cells and/or fibroblasts and/or adipose tissue-derived cells and/or other tissues resident cells and/or activated cell type used for cell therapy and applying the activated macrophages or the activated mesenchymal stem cells or the activated cell type used for cell therapy to the heart. In some embodiments the chemotherapy agent is a combination of paclitaxel and anakinra or anakinra alone. In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues resident cells and/or any other cell type that can be used in cell therapy that are activated by a chemotherapy agent, wherein the mesenchymal stem cells and/or the macrophages and/or T cells and/or fibroblasts and/or neural tissue cells (such as astrocytes and glia cells) and/or adipose tissue-derived cells and/or other tissues resident cells and/or the cell type that is used in cell therapy that are activated by a specific chemotherapy agent were separated from a supernatant and wherein the supernatant is used as a therapy can be used in the method of treating described above.

In some embodiments of the invention, there is provided a method of treating renal injury or nephropathy comprising the steps of contacting macrophage or mesenchymal stem cells or any other cell type used for cell therapy with a chemotherapy agent, so as to provide activated macrophages or activated mesenchymal stem cells and/or T cells and/or fibroblasts and/or neural tissue cells (such as astrocytes and glia cells) and/or adipose tissue-derived cells and/or other tissues resident cells and/or activated cell type used for cell therapy, and applying the activated macrophages or the activated mesenchymal stem cells and/or neural tissue cells (such as astrocytes and glia cells) and/or adipose tissue-derived cells and/or other tissues resident cells and/or the activated cell type used for cell therapy to the kidney. In some embodiments the chemotherapy agent is cisplatin.

In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues resident cells and/or any other cell type that can be used in cell therapy that are activated by a chemotherapy agent, wherein the mesenchymal stem cells and/or the macrophages and/or T cells and/or fibroblasts and/or and/or neural tissue cells (such as astrocytes and glia cells) and/or adipose tissue-derived cells and/or other tissues resident cells the cell type that is used in cell therapy that are activated by a specific chemotherapy agent were separated from a supernatant and wherein the supernatant is used as a therapy can be used in the method of treating described above.

In some embodiments of the invention, there is provided a method of treating an inflammatory bowel disease (IBD), such as Crohn's disease or ulcerative colitis, comprising the steps of contacting macrophages and/or mesenchymal stem cells and/or T cells and/or fibroblasts and/or adipose tissue-derived cells and/or other tissues resident cells and/or any other cell type used for cell therapy with a chemotherapy agent, so as to provide activated macrophages and/or activated mesenchymal stem cells, and/or T cells and/or fibroblasts and/or adipose tissue-derived cells and/or other tissues resident cells and/or activated cell type used for cell therapy and applying the activated macrophages or the activated mesenchymal stem cells and/or macrophages and/or T cells and/or fibroblasts and/or adipose tissue-derived cells and/or other tissues' resident cells or the activated cell type used for cell therapy to the GI tract or intestines. In some embodiments the chemotherapy agent is 5-FU.

In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues resident cells and/or any other cell type that can be used in cell therapy that are activated by a chemotherapy agent, wherein the mesenchymal stem cells and/or the macrophages and/or T cells and/or fibroblasts and/or neural tissue cells (such as astrocytes and glia cells) and/or adipose tissue-derived cells and/or other tissues resident cells and/or the cell type that is used in cell therapy that are activated by a specific chemotherapy agent were separated from a supernatant and wherein the supernatant is used as a therapy can be used in the method of treating described above.

In some embodiments of the invention, there is provided a method of treating a skin wound such as burns, diabetic lesion and the like, comprising the steps of contacting macrophages and/or mesenchymal stem cells and/or T cells and/or fibroblasts and/or adipose tissue-derived cells and/or other tissues' resident cells and/or any other cell type used for cell therapy with a chemotherapy agent, so as to provide activated macrophages or activated mesenchymal cell and/or T cells and/or fibroblasts and/or adipose tissue-derived cells and/or other tissues' resident cells and/or activated cell type used for cell therapy, and applying the activated macrophages and/or T cells and/or fibroblasts and/or the activated mesenchymal stem cells and/or adipose tissue-derived cells and/or other tissues' resident cells or the activated cell type used for cell therapy to the skin in a location where the wound can be repaired. In some embodiments, the chemotherapy agent is dacarbazine. In some embodiments, an activating composition that comprises mesenchymal stem cells and/or macrophages and/or T cells and/or fibroblasts and/or adipose tissue-derived cells and/or other tissues resident cells and/or any other cell type that can be used in cell therapy that are activated by a chemotherapy agent, wherein the mesenchymal stem cells and/or the macrophages and/or T cells and/or fibroblasts and/or adipose tissue-derived cells and/or other tissues' resident cells and/or the cell type that is used in cell therapy that are activated by a specific chemotherapy agent were separated from a supernatant and wherein the supernatant is used as a therapy can be used in the method of treating described above.

In some embodiments of the invention, there is provided a method of treating a neurodegenerative disease such as ALS, Parkinson's disease, Alzheimer's disease, and the like, comprising the steps of contacting macrophages and/or mesenchymal stem cells and/or T cells and/or fibroblasts and/or neural tissue cells (such as astrocytes and glia cells) and/or adipose tissue-derived cells and/or other tissues resident cells and/or any other cell type used for cell therapy with a chemotherapy agent, so as to provide activated macrophages and/or activated mesenchymal stem cells and/or neural tissue cells (such as astrocytes and glia cells) and/or adipose tissue-derived cells and/or other tissues' resident cells or other cell type used for cell therapy and applying the activated macrophages and/or T cells and/or fibroblasts and/or the activated mesenchymal stem cell and/or neural tissue cells (such as astrocytes and glia cells) and/or adipose tissue-derived cells and/or other tissues resident cells and/or other activated cell type used for cell therapy to the damaged area in the brain. In some embodiments the chemotherapy agent is temozolomide.

In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues' resident cells and/or any other cell type that can be used in cell therapy that are activated by a chemotherapy agent, wherein the mesenchymal stem cells and/or the macrophages and/or T cells and/or fibroblasts and/or neural tissue cells (such as astrocytes and glia cells) and/or adipose tissue-derived cells and/or other tissues' resident cells and/or the cell type that is used in cell therapy that are activated by a specific chemotherapy agent were separated from a supernatant and wherein the supernatant is used as a therapy can be used in the method of treating described above.

In some embodiments of the invention, there is provided a method of treating aging related conditions comprising the steps of contacting macrophages and/or mesenchymal stem cells and/or T cells and/or fibroblasts and/or neural tissue cells (such as astrocytes and glia cells) and/or adipose tissue-derived cells and/or other tissues' resident cells or any other cell type used for cell therapy with a chemotherapy agent, so as to provide activated macrophages and/or activated mesenchymal stem cells and/or T cells and/or fibroblasts and/or neural tissue cells (such as astrocytes and glia cells) and/or adipose tissue-derived cells and/or other tissues' resident cells or activated other cell type that is used for cell therapy and applying the activated macrophages and/or the activated mesenchymal stem cells and/or T cells and/or fibroblasts and/or neural tissue cells (such as astrocytes and glia cells) and/or adipose tissue-derived cells and/or other tissues' resident cells or the activated cell type that is used for cell therapy to the damaged area in the brain. In some embodiments the chemotherapy agent is temozolomide.

In some embodiments, an activating composition that comprises mesenchymal stem cells and/or macrophages and/or T cells and/or fibroblasts and/or neural tissue cells (such as astrocytes and glia cells) and/or adipose tissue-derived cells and/or other tissues' resident cells and/or any other cell type that can be used in cell therapy that are activated by a chemotherapy agent, wherein the mesenchymal stem cells and/or the macrophages and/or T cells and/or fibroblasts and/or neural tissue cells (such as astrocytes and glia cells) and/or adipose tissue-derived cells and/or other tissues' resident cells and/or the cell type that is used in cell therapy that are activated by a specific chemotherapy agent were separated from a conditioned medium and wherein the conditioned medium is used as a therapy can be used in the method of treating described above.

In some embodiments of the invention, there is provided a method of treating autoimmune related conditions comprising the steps of contacting macrophages and/or mesenchymal stem cells and/or T cells and/or fibroblasts and/or neural tissue cells (such as astrocytes and glia cells) and/or adipose tissue-derived cells and/or other tissues' resident cells or any other cell type used for cell therapy with a chemotherapy agent, so as to provide activated macrophages and/or activated mesenchymal stem cells and/or T cells and/or fibroblasts and/or neural tissue cells (such as astrocytes and glia cells) and/or adipose tissue-derived cells and/or other tissues' resident cells or activated other cell type that is used for cell therapy and applying the activated macrophages and/or the activated mesenchymal stem cells and/or T cells and/or fibroblasts and/or neural tissue cells (such as astrocytes and glia cells) and/or adipose tissue-derived cells and/or other tissues' resident cells or the activated cell type that is used for cell therapy to the damaged area in the brain. In some embodiments the chemotherapy agent is methotrexate.

TABLE 1

| Different chemotherapies can be used for activating cells for various indications. | | | |
| --- | --- | --- | --- |
| Chemotherapy | Application | Organ | Clinical effects |
| Gemcitabine | Pancreatitis | Pancreas | Immunosuppression, tissue remodeling |

TABLE 1-continued

Different chemotherapies can be used for activating cells for various indications.

| Chemotherapy | Application | Organ | Clinical effects |
|---|---|---|---|
| Paclitaxel | Lung injury, | Breast, ovaries, lungs | Lymph- and angiogenesis, tissue regeneration |
| Paclitaxel + anakinra | MI, heart failure | Heart | Tissue regeneration, angiogenesis, prevention of fibrosis |
| Cisplatin | Renal injury, nephropathy | Kidney, lungs | Immunosuppression, tissue regeneration |
| 5-FU | Inflammatory bowel diseases (Crohn's disease, ulcerative colitis) | GI tract, intestine | Inhibition of Inflammation, healing, angiogenesis |
| Dacarbazine | Skin wounds, burns, diabetic lesions | Skin | Wound healing |
| Temozolomide | ALS, neurodegeneration | Brain | Stem cells, neural differentiation |
| Bortezomib | Severe burns, Chemotherapy, radiation, diabetes, malnutrition | Multiple organs including skin, pancreas, GI tract | Pro-inflammatory response, increase immune activity, replenish bone marrow cells. |

TABLE 2

Secretome of mesenchymal stem cells activated with gemcitabine chemotherapy (protein expression in the conditioned medium of MSC is presented as a fold increase between naive and gemcitabine-activated MSC)

| Analyte | Fold increase (MSCs) |
|---|---|
| DPPIV (CD26) | 83.150 |
| CD14 | 45.850 |
| TNFRSF8 (CD30) | 36.235 |
| IL-2 | 31.215 |
| IP-10 (CXCL10) | 22.545 |
| I-TAC (CXCL11) | 19.345 |
| IL-15 | 17.385 |
| IL-1ra | 16.005 |
| IL-3 | 14.280 |
| IL-16 | 13.930 |
| BAFF | 13.690 |
| MIP-3b (CCL19, ELC) | 13.120 |
| RLN2 | 12.890 |
| G-CSF (CSF3) | 12.470 |
| IL-31 | 11.815 |
| C5/C5a | 11.340 |
| IL-13 | 10.917 |
| MIP-3a (CCL20, LARC) | 10.510 |
| IL-34 | 10.195 |
| BDNF | 9.705 |
| EGF | 8.079 |
| IL-1b | 7.854 |
| Cripto-1 | 7.602 |
| IL-19 | 7.470 |
| Myeloperoxidase (MPO) | 7.408 |
| MIG (CXCL9) | 7.404 |
| IL-32a/b/g | 7.301 |
| IL-23 (SGRF) | 7.090 |
| IL-10 | 5.900 |
| TGF-a | 4.874 |
| ICAM-1 (CD54) | 4.366 |
| MIP-1a/MIP-1b (CCL3/CCL4) | 4.305 |
| IL33 | 3.895 |
| TNF-a | 3.504 |
| MMP-9 (Gelatinase B) | 3.396 |
| IFN-g | 3.121 |
| RAGE | 3.117 |
| CXCL4 (PF4) | 2.961 |
| GM-CSF (CSF2) | 2.945 |
| IL-4 | 2.880 |
| IL-8 (CXCL8) | 2.797 |

TABLE 2-continued

Secretome of mesenchymal stem cells activated with gemcitabine chemotherapy (protein expression in the conditioned medium of MSC is presented as a fold increase between naive and gemcitabine-activated MSC)

| Analyte | Fold increase (MSCs) |
|---|---|
| Leptin (OB) | 2.780 |
| IGFBP-2 | 2.765 |
| NGAL (LCN2) | 2.755 |
| ST2 (IL-1 R4, IL1RL1) | 2.627 |
| FGFb | 2.589 |
| RBP4 | 2.584 |
| Cystatin C | 2.576 |
| FLT-3L | 2.520 |
| IL-27 | 2.508 |
| PSA (KLK3) | 2.467 |
| IL-18 Bpa | 2.446 |
| IL-1a | 2.419 |
| IL-22 (IL-TIF) | 2.309 |
| SHBG (ABP) | 2.302 |
| Ang-2 | 2.113 |
| TFF3 (ITF) | 1.966 |
| MCP-3 (CCL7, MARC) | 1.922 |
| IL-12 p70 | 1.871 |
| IL-6 | 1.752 |
| TfR (CD71) | 1.738 |
| Aggrecan I | 1.626 |
| Resistin (ADSF, FIZZ3) | 1.586 |
| IL-11 | 1.571 |
| CCL5 (RANTES) | 1.555 |
| OPN | 1.542 |
| Endoglin (CD105) | 1.508 |
| uPAR | 1.487 |
| GH (Somatotropin) | 1.485 |
| CRP | 1.471 |
| GDF-15 (MIC-1) | 1.463 |
| FGF-19 | 1.452 |
| FasL (CD178, CD95L) | 1.396 |
| EMMPRIN (CD147) | 1.356 |
| Ang-1 | 1.349 |
| VEGF-A | 1.345 |
| THBS1 (TSP-1) | 1.322 |
| FGF-7 | 1.223 |
| MIF | 1.194 |
| CXCL5 | 1.192 |
| Adispin (CFD) | 1.138 |
| Vit D BP | 1.127 |

TABLE 2-continued

Secretome of mesenchymal stem cells activated with
gemcitabine chemotherapy (protein expression in the
conditioned medium of MSC is presented as a fold increase
between naive and gemcitabine-activated MSC)

| Analyte | Fold increase (MSCs) |
|---|---|
| Dkk-1 | 1.124 |
| PDGF-AA | 1.122 |
| SDF-1a (CXCL12) | 1.083 |
| IGFBP-3 | 1.065 |
| M-CSF (CSF1) | 1.058 |
| Angiogenin | 1.056 |
| MCP-1 (CCL2, MCAF) | 1.040 |
| IL-17A (CTLA8) | 1.021 |
| PTX3 (TSG-14) | 1.015 |
| Serpin E1 (PAI-I, Nexin) | 0.987 |
| LIF | 0.000 |
| CHI3L1 | −1.029 |
| Adiponectin | −1.27 |
| CD40L (TRAP) | −1.32 |
| GRO-a (CXCL1) | −14.12 |
| HGF | −1.11 |
| IL-24 | −1.23 |
| IL-5 | −1.21 |
| PDGF-AB/BB | −1.56 |
| TARC (CCL17) | −1.27 |

In some embodiments, there is provided a method for preparing a medicament for treating a damaged tissue comprising the steps of:

analyzing a secretome from a conditioned medium from mesenchymal stem cells and/or macrophages and/or T cells and/or fibroblasts and/or neural cells and/or adipose cells that were activated by an anticancer drug;

preparing a composition that includes a combination of two or more active ingredients identified in the secretome;

assessing the efficiency of the composition.

In some embodiments, the ratio between the two or more of the active ingredients is about the same ratio as was identified in the secretome.

The method can be used on a personal levels i.e. different cells activated by different anticancer agents will result in different active ingredients and/or different ratios there between. Thus, personal composition can be prepared for each person.

Thus, one may treat a disease or disorder or a condition associated with tissue damage by using a conditioned media from mesenchymal stem cells and/or macrophages and/or T cells and/or fibroblasts and/or neural cells and/or adipose cells that were activated by an anticancer drug or by identifying the ingredients in a secretome thereof, determining the ratio therebetween and preparing such a composition for use as a medicament.

EXAMPLES

Materials and Methods

Cell Cultures

Human pancreatic adenocarcinoma cell line (PANC1) was purchased from the American Type Culture Collection (ATCC) and was cultured in Dulbecco's modified Eagle's medium (DMEM). Culture media were supplemented with 10% FCS, in the presence of 1% penicillin-streptomycin, 1% sodium pyruvate, and 1% L-glutamine at 37° C. in a 5% CO2 environment for no more than 6 months after being thawed from original stocks.

For the analysis of CSC enrichment, PANC1 cells were cultured in serum-free medium (control), CM derived from untreated or chemotherapy-educated MSC, or were co-cultured in serum-free medium with untreated or chemotherapy-educated MSC in a 10:1 ratio. In some groups, serum-free medium was supplemented with anti-hCXCL10 (1 μg/ml, R&D systems). After 3 days, cultures were evaluated for CSC enrichment using immunophenotype analysis as described below.

The Generation of Chemotherapy-Educated MSC or MSC-Derived Conditioned Medium

Human bone marrow MSCs (LONZA, Switzerland) were cultured in minimum essential medium-alpha (αMEM) supplemented with 10% FBS 1% L-glutamine, 1% sodium-pyruvate, and 1% streptomycin. Medium was replaced every 3 days, and cells were maintained in culture for up to 7 passages.

In some cases, human MSCs isolated from bone marrow aspirates, of healthy patients were used and cultured in culture dishes in minimum essential medium-alpha (αMEM) supplemented with 10% FBS 1% L-glutamine, 1% sodium-pyruvate, and 1% streptomycin. The purification of MSCs was performed based on their adhesion abilities to plastic culture dishes. Medium was changed every 3 days until the hematopoietic cells were washed away, leaving the adhered MSCs homogenous culture. The achieved MSCs were expanded and passaged, while cells up to passage 7 were used for the experiments.

In some cases, murine MSCs were isolated from bone marrow aspirates and cultured in culture dishes in minimum essential medium-alpha (αMEM) supplemented with 10% FBS 1% L-glutamine, 1% sodium-pyruvate, and 1% streptomycin were used. The purification of MSCs was performed based on their adhesion abilities to plastic culture dishes. Medium was changed every 3 days until the hematopoietic cells were washed away, leaving the adhered MSCs homogenous culture. The achieved murine MSCs were expanded and passaged, while cells up to passage 10 were used for the experiments.

To generate chemotherapy-educated MSCs, cultured MSCs were exposed to paclitaxel (100 nM), gemcitabine (10 nM), cisplatin (10 μM) or vehicle control for 24 hours. To generate MSC-derived CM, the chemotherapy-educated MSCs (as above) were re-seeded in serum-free medium at a concentration of 1×105 cells/ml. After 72 hours, CM was collected.

Animal Models, Treatments, and Live Imaging

The use of animals and experimental protocols were approved by the Animal Care and Use Committee of the Technion. Human PANC1 ($5 \times 10^6$ cells) were subcutaneously injected into the flank of eight-to-ten-week-old CB.17 female SCID mice (Harlan, Israel). Tumor size was assessed regularly with Vernier calipers using the formula width$^2$× length×0.5. Mice were treated with 500 mg/kg gemcitabine (Eli Lilly Ltd.) or vehicle control.

For in vivo wound healing assay, a small (0.5 cm) incision was performed on the back of eight-to-ten-week-old BALB/c mice. On the surgery day, mice were externally treated with the conditioned medium of untreated or gemcitabine-activated MSCs or left untreated. Wound size was monitored daily and assessed with Vernier calipers. Mice were randomly grouped before the procedure.

Matrigel Plug Assay

Matrigel (0.5 ml) that contained precipitated conditioned-medium of either untreated MSCs or MSCs pre-exposed to gemcitabine, paclitaxel or cisplatin, was injected subcutaneously into each flank of a BALB/c female mouse, 8-10 weeks of age, (n=5 mice/group). Plugs were removed 10 days later, and subsequently prepared for either histological evaluation, or flow cytometric analysis following single cell suspension as previously described (13). Cell suspensions were immunostained with antibody mixtures to detect cell types defined by their surface markers as follows: ECs: CD31+/VEGFR2+/CD45−; MDSCs: Gr-1+/CD11b+/CD45+; M1 macrophages: F4/80+, CD11b+, CD11c+, CD206−; M2 macrophages: F4/80+, CD11b+, CD11c+, CD206+; NK cells NKp46+, CD45+; B cells CD45R (B220)+, CD45+; and T cells CD3ε+, CD45+. All monoclonal antibodies were purchased from Biolegend, BD Biosciences, R&D systems, and Macs Militenyi Biotec, and used according to the manufacturers' instructions. The monoclonal antibodies were purchased conjugated with the following fluorochromes: Gr-1-Fluorescein isothiocyanate (FITC), VEGFR2-Phycoerythrin (PE), CD11b-Peridinin-chlorophyll proteins (PerCP), CD31-FITC, and CD45-APC-Cy7, F4/80-PE, CD11c-APC-Cy7, CD206-BV421, NKp46-APC, CD45R (B220)-BV605, CD3ε-Pacific blue. When necessary, after red blood cell lysis, cell suspensions were analyzed by CyAn ADP Flow cytometer and Summit v4.3 software (Beckman Coulter). An acquisition of at least 100,000 cells per sample was performed. Analyses were considered informative when an adequate number of events (typically 50-150) were collected in the EC, MDSC, macrophages, B cell or T cell enumeration gates in untreated control animals. Percentages of stained cells were determined and compared with appropriate negative controls. Positive staining was defined as being greater than non-specific background staining, and 7-aminoactinomycin D (7AAD) was used to distinguish apoptotic and dead cells from viable cells.

Evaluation of the Effect of MSC on Cytotoxic T Cell Activity

Cytotoxic T cell activity was evaluated using a mouse T cell activation kit (Miltenyi Biotec, Germany) in accordance with the manufacturer's instructions. Briefly, splenocytes ($10^7$) from naïve BALB/c mice were cultured for 24 hours at 37° C. in the presence or absence of anti-mouse CD3ε and CD28 biotinylated beads ($10^6$ beads/sample) in the presence or absence of the conditioned medium of naïve MSC or MSC pre-exposed with different chemotherapies (gemcitabine 10 nM, paclitaxel 100 nM, or cisplatin 10 μM). The beads mimic antigen-presenting cells and activate resting T cells. Subsequently, cells were centrifuged at 470×g for 5 min at room temperature. Cell pellets were resuspended in PBS, and the levels of total CD8$^+$ T cells and activated T cells (CD8$^+$/CD25$^+$ or CD8$^+$/CD107a$^+$), were quantified by flow cytometry.

Scratch Wound Assay

The in vitro scratch wound assay was performed using PANC1 cells that were cultured in 96 well flat transparent plates (Thermo Fisher Scientific, Waltham, MA) in DMEM supplemented with 10% FCS. The cells were starved in serum-free DMEM for 16 hours before they were assayed. Before the scratch was performed, the cells were incubated with CM of untreated MSCs or MSC exposed to paclitaxel (100 nM), gemcitabine (10 nM), cisplatin (10 μM). Time-Lapse images of cell migration were captured using IncuCyte ZOOM HD/2CLR system, per ×100 objective-field and analyzed with IncuCyte ZOOM 2016B software (Essenbioscience, Ann Arbor, MI).

Modified Boyden Chamber Assay

The effects of CM of untreated MSCs or MSC exposed to paclitaxel, gemcitabine, cisplatin on migration properties of PANC1 cell cultures were evaluated in fibronectin-coated Boyden chambers, using a previously described protocol (14, 15). Briefly, serum-starved cells ($2 \times 10^5$ cells in 0.2 ml serum free DMEM medium) were added to the upper compartment of the chamber that was coated with 50 μl fibronectin (10 μg/ml). The lower compartment was filled with CM from MSCs either untreated or pretreated with different chemotherapies as described above. After 24 hours, cells that migrated to the bottom filter, were stained with crystal violet and counted under an inverted microscope (Leica DMIL LED) per ×100 objective-field. All experiments were performed in triplicate.

Immunostaining

Tumors or Matrigels were embedded in O.C.T. (Sakura, Japan) and subsequently frozen at −80° C. Tissue sections (10 μm thick) were prepared using Leica CM 1950 microtome (Leica, Germany). Sections were fixed in cold acetone for 15 minutes. CSCs were stained with PE-conjugated antibodies against human prominin-1 (CD133, 1:250, Macs MiltenyiBiotec). To identify MSCs, sections were stained with FITC-conjugated antibodies against endoglin (CD105) and APC-conjugated antibodies against CD44 (1:200, BD Biosciences). Tumor sections were analyzed with a camera attached to an inverted microscope (Leica CTR 6000) using Leica Application suite Version 3.4.0 software or a LSM 700 Zeiss confocal microscope (Zeiss, Germany). Nuclei were stained with DAPI (Electron Microscopy Sciences, PA, USA).

Cytokine Array

CM from gemcitabine-educated or control MSCs were applied to a proteome profiler human XL cytokine array (ARY022B, R&D systems, MN) in accordance with the manufacturer's instruction. The signals corresponding to each factor in the array were quantified by densitometry analysis. The ratio between the expression levels of the various factors secreted by gemcitabine-educated and untreated MSCs was calculated.

Statistical Analysis

Data are expressed as mean±standard deviation (SD). The statistical significance of differences was assessed by one-way ANOVA, followed by Tukey ad hoc statistical test using GraphPad Prism 5 software (La Jolla, CA). Student t-test was used in some experiments when comparing only two groups. Differences between all groups were compared with each other, and were considered significant at p values below 0.05.

Results

Chemotherapy-Activated MSCs Enrich for Stem Cells

MSCs are one of the major candidates for tissue regeneration and cell therapy due to their high proliferative potential and ability to differentiate to main mesenchymal tissues. Moreover, MSCs have been shown to contribute to systemic resistance to chemotherapy in solid tumors by the secretion of two specific fatty acids following exposure to platinum-based cytotoxic agents. These fatty acids indirectly protect colon and lung carcinoma cells from the cytotoxic effects of the chemotherapy. However, the interactions of MSCs with tissue-resident stem cells are not yet clear, especially following chemotherapy. To this end we analyzed subcutaneous pancreatic tumors, generated by injection of $5 \times 10^6$ PANC1 cells to flanks of 8- to 10-week-old SCID mice. When tumors reached 500 mm$^3$, mice were treated with 500 mg/kg gemcitabine and after 3 days mice were removed and sacrified. Immunostaining of the tumors for MSCs and CSCs was demonstrated following gemcitabine therapy. Specifically, MSCs home to tumors and locate in close proximity to CSCs, when compared to untreated control (FIG. 1A). In addition, FIG. 1B demonstrates that chemotherapy induced massive recruitment of MSCs to pancreatic tumors, which is similar to MSC infiltration to damaged tissue sites, as was previously shown. Furthermore, to study, whether MSCs contribute to CSC repopulation, we applied CM of untreated MSCs or gemcitabine-educated MSCs and CSC enrichment was evaluated using phenotypic characterization by flow cytometry, as described in Materials and Methods. We showed that activation of MSCs with chemotherapy resulted in significant enrichment of CSCs when compared to the effect of untreated MSCs. Secretome analysis of gemcitabine-activated MSCs revealed that CXCL10 secretion is highly elevated following chemotherapy treatment, relatively to untreated MSCs, as presented in Table 1. We showed that CXCL10 promoted CSC enrichment by binding to CXCR3 receptor and consecutive induction of STAT3 signaling. CXCL10 neutralization with anti-CXCL10 antibody, canceled the enrichment effect of chemotherapy-activated MSCs on CSC (FIG. 1C). These results were published in January in Cancer Research (6). Taken together, our results demonstrate that following chemotherapy activation MSC contribute to tissue-residing CSC.

Chemotherapy-Activated MSCs Promote Immunosuppression and Induce Angiogenesis

MSCs are known for their ability to home to injured sites and promote tissue regeneration. Moreover, MSCs secrete a whole milieu of cytokines and chemokines including TGFβ, IL-6, $PGE_2$, IDO, LIF to modulate recruitment of various hematopoietic cell types which modulate tissue structure). To test these abilities in our experimental conditions, Matrigel plug assay was performed. To this end, Matrigel plugs which contained CM generated from untreated or gemcitabine-educated MSCs were implanted into the flanks of 8- to 10-weeks-old Balb/c mice. After 10 days, plugs were removed and prepared as single cell suspension. The cells from the plugs were phenotypically analyzed by flow cytometry to identify cells that were recruited to the plugs. We found that CM from gemcitabine treated MSCs induced the recruitment of endothelial cells, suggesting an increased angiogenic potential following gemcitabine therapy. In addition, the colonization of most immune populations, including macrophages, NK cells, T cells and B cells was significantly decreased in Matrigel plugs with CM from gemcitabine-activated MSC when compared to plugs containing CM of control MSCs (FIG. 2A-B). To further elaborate the immunomodulatory effects of chemotherapy-exposed MSCs, T cell activation assay by applying the CM of naïve or chemotherapy-activated MSC on splenocytes extracted from naïve Balb/c mice was performed. As a result, chemotherapy-activated MSC significantly decreased the total amount of CD8 T cells and suppressed the activation of cytotoxic T cells (FIG. 3). Overall, the results provide an additional support that in tumors, similar to damaged tissue, MSC obtain strong regenerative abilities facilitated by increased angiogenesis and an induction of immunosuppression in order to increase overall tissue repair.

Chemotherapy Activated MSCs Increase Effective Tissue Repair

Based on the enhanced proangiogenic and immunosuppressive properties of chemotherapy-activated MSCs, the ability of MSC to heal wounds was assessed. To this end, the effect of MSCs on the migratory properties of other cells by performing a Modified Boyden chamber assay was tested, as described in Material and Methods. To do so, PANC1 ($2\times10^6$ cells) were cultured in the upper chamber of the well, whereas the lower chamber was loaded with the CM of chemotherapy-activated MSCs or CM of untreated MSCs.

After 24 hours, the cells that migrated to the lower side of the chamber, were fixed and subsequently stained with crystal violet. It was found that CM of gemcitabine-activated MSCs dramatically increased the migration properties of PANC1 cells, compared to control group. Interestingly, CM generated from MSCs exposed to other cytotoxic agents such as paclitaxel and cisplatin did not affect migration abilities of the cells (FIG. 4A). In addition, scratch wound assay was generated to further demonstrate the regenerative potential of chemotherapy-activated MSCs. Cells treated with the CM of gemcitabine-educated MSC closed the gap faster than untreated control cells or cells exposed to CM of untreated MSCs (FIG. 4B-C). In parallel with the migration assay results, wound closure time of cells treated with CM from MSC exposed to PTX or cisplatin was similar to the control groups.

Next, the wound healing properties of chemotherapy-activated MSCs were tested in vivo. For this purpose, 0.5 cm incision was performed on the back of BALB/c mice. After 24 hours, the mice were treated externally with the conditioned medium of untreated MSCs or MSC pre-exposed to 10 nM gemcitabine. Control mice were left untreated. Wound healing was monitored until the complete closure of the wound. The results showed that wound healing in mice treated with gemcitabine-activated MSCs was the fastest comparing to control groups (FIG. 4D). Taken together, our results demonstrate that chemotherapy-educated MSC drastically induces MSCs regenerative and wound healing characteristics, therefore contributing to damage repair.

Example 2

Chemotherapy Activated MSCs for Use in Treating Lung Fibrosis

Bronchoalveolar Lavage

All animal studies and animal experimental protocols were approved by the Animal Care and Use Committee of the Technion. Murine pulmonary fibrosis model was established by the administration of a single dose of bleomycin, given intratracheally (IT), as shown in Van Hoecke, L., et al., Bronchoalveolar Lavage of Murine Lungs to Analyze Inflammatory Cell Infiltration. J Vis Exp, 2017(123) and Cox, T. R., et al., LOX-mediated collagen crosslinking is responsible for fibrosis-enhanced metastasis. Cancer Res, 2013. 73(6): p. 1721-32.

Briefly, 10-week-old female BALB/c mice were administrated intratracheally (IT) with 0.04 units of bleomycin or treated with vehicle control. After one week, mice were either left untreated or administered IT with conditioned medium of control-MSC or chemo-activated MSC. This treatment (70 μl of the conditioned medium of activated MSC, as described above in the Methods Section) was given for a week period, every other day. Fourteen days after bleomycin administration, bronchoalveolar lavage (BAL) was performed by washing the lungs with Hank's balanced salt solution (HBSS) supplemented with 100 uM ethylenediaminetetraacetic acid (EDTA, both from Biological industries ltd, Israel) and was analyzed using flow cytometry for pulmonary inflammatory cell infiltration. Consequently, lungs were harvested, fixated, and processed for histology. Evaluation of Inflammatory Cell Types in Bronchoalveolar Lavage (BAL) Using Flow Cytometry To assess the various immune cell types after BAL procedure, cells were extracted from bronchoalveolar liquid of bleomycin-treated or control mice. The cells were then immunostained and analyzed to define various innate and adaptive immune cell populations, including T cells (CD4+ and CD8+), B cells (B220), macrophages (CD11b+ F4/80+, CD11c±, CD206±), NK cells (NKp46), and myeloid derived suppressor cells (MDSC, CD11b+, Ly6G±, Ly6C±). All monoclonal antibodies were purchased from BioLegend (San Diego, CA, USA) and used in accordance with the manufacturer's instructions. Sample acquisition was performed using LSR Fortessa flow analyzing system (BD Biosciences, San Jose, CA, USA) followed by analysis using the FlowJo X software (FlowJo, LLC, Ashland, OR, USA).

Histology

Lungs from control or treated mice were harvested at endpoint and subsequently were fixated with PFA. Paraffin-embedded lung tissues were sectioned and stained with Hematoxylin and Eosin (H&E) solution. To assess collagen content representing fibrosis, lung sections were stained with Sirius Red solution (marked in red).

Results

Figure 5:
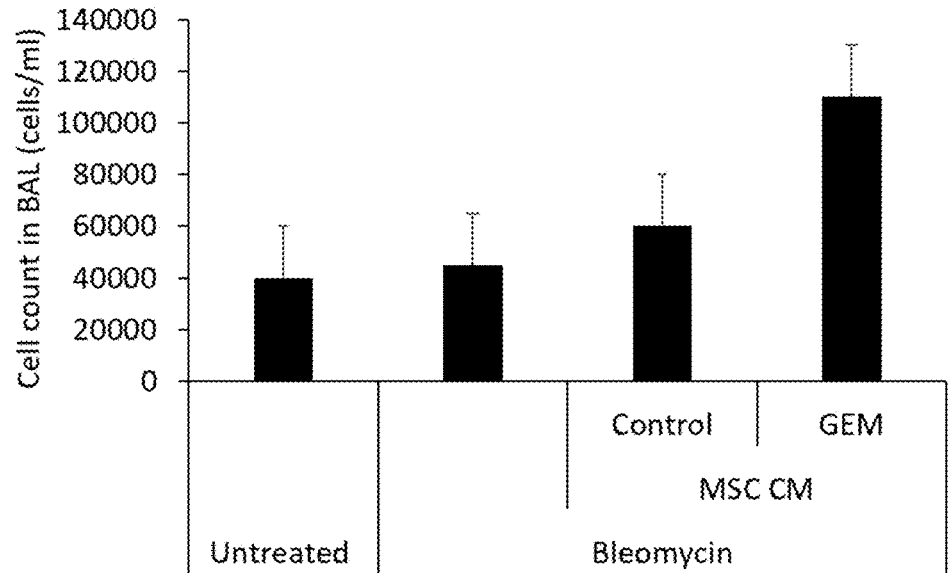
FIG. 5 is a graph showing the homing of cells to lungs of mice induced with lung fibrosis Ten week old Balb/c mice were intratracheally administered with 0.04 units of Bleomycin (Baxter Oncology GmbH, Germany) or treated with vehicle control. After one week, mice were either left untreated or administered intratracheal (IT) with CM of control-MSC or chemo-activated MSC. Treatment was given for a week, every other day. Fourteen days after Bleomycin administration, bronchoalveolar lavage (BAL) was performed and cells were counted. The number of cells from BAL is shown.
Figure 6A:
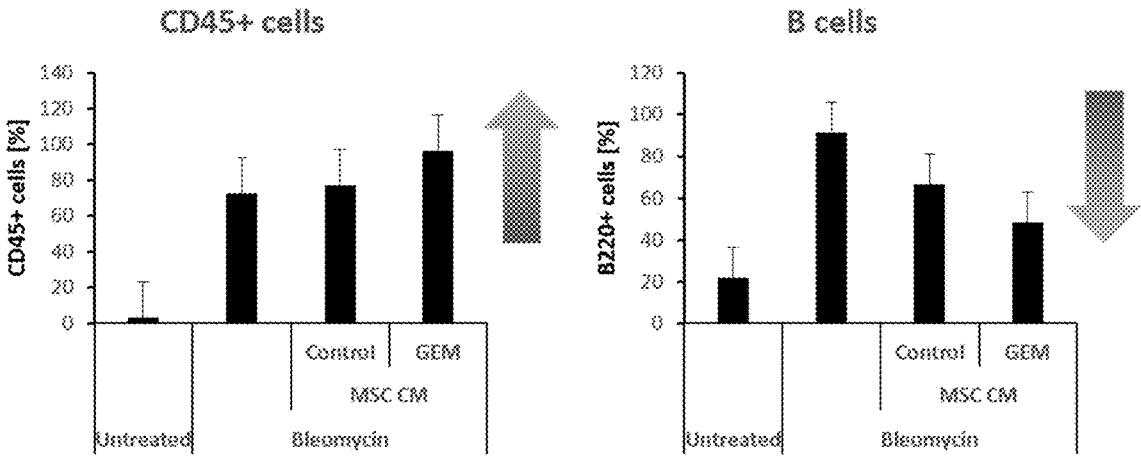
As shown in FIGS. 6A-D, the percentage of pro-inflammatory cells was decreased while the percentage of anti-inflammatory cells was increased, therefore demonstrating a tissue regeneration process.
Figure 6B:
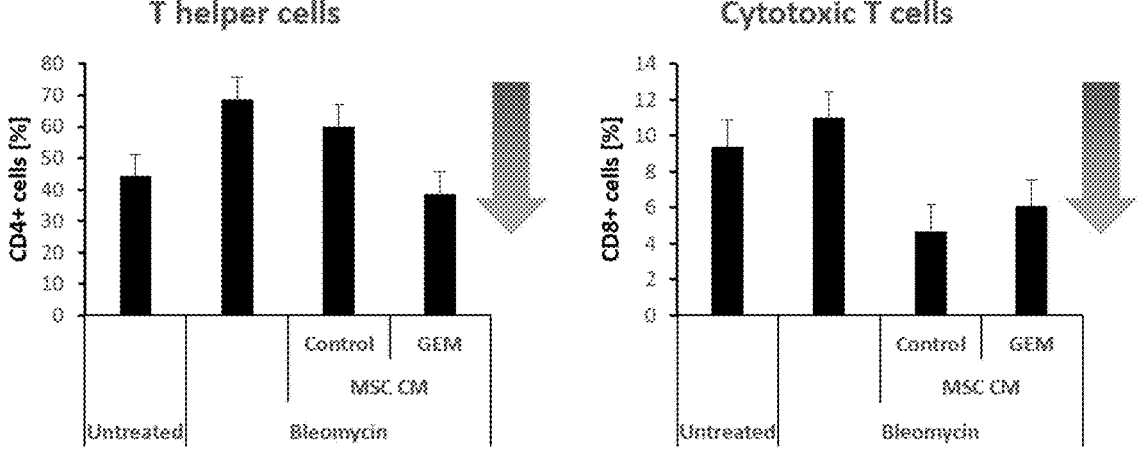
Figure 6C:
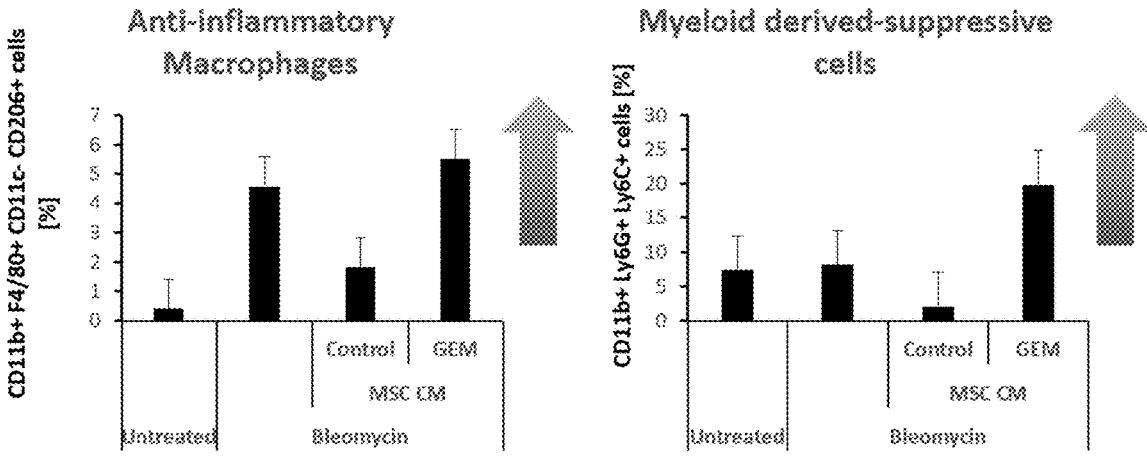
Figure 6D:
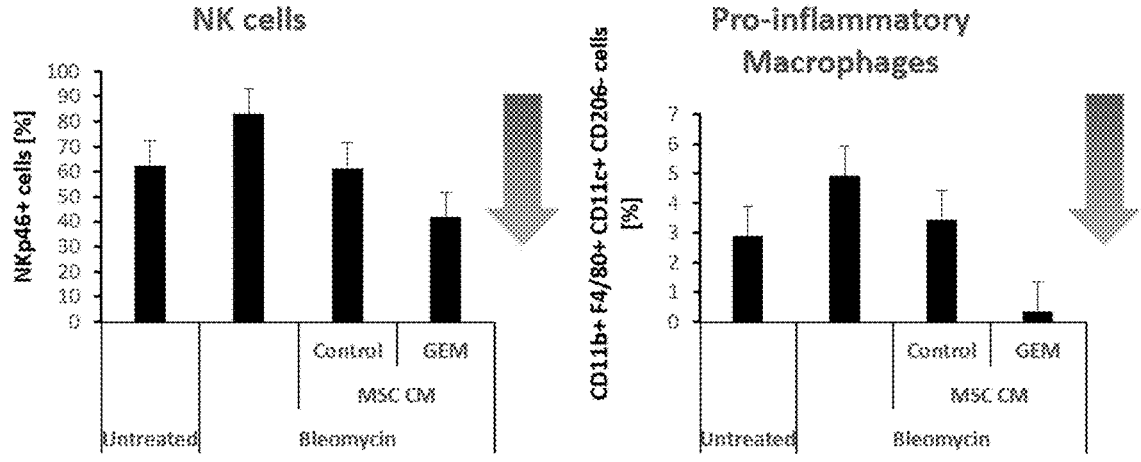

Tissue injury often results in developing of scar tissue and fibrosis, when functional tissue is massively replaced with rough connective tissue leading to an impaired physiological function. Specifically, pulmonary fibrosis (PF) is an interstitial lung disease, the cause of which in most cases is unknown. Lung injury, inflammatory processes, pulmonary diseases, exposure to radiation and chemicals may induce PF, and its mortality rates are growing. In experimental animal settings, bleomycin is a widely used agent for induction of lung fibrosis model. Therefore, a bleomycin-induced fibrosis model was implemented to assess the efficiency of the proposed stem cell-based therapy for preventing and healing fibrosis. Specifically, the assessment of the cell number in BAL samples demonstrated that the administration of condition medium (CM) of chemo-activated MSCs as explained in the methods section above, in the bleomycin-treated lungs enhanced recruitment and homing of cells into the lungs, when compared to the control groups (FIG. 5). Specifically, lung fibrosis-induced mice treated with CM of chemo-activated MSC compared to all other groups resulted in an increase in CD45-positive cells. These cells were composed of an increased percentage of anti-inflammatory macrophages and myeloid derived suppressor cells—both of which represent tissue regeneration and growth—as well as decreased percentage of pro-inflammatory macrophages, T cells, B cells and NK cells—all of which represent tissue inflammation which inhibits tissue regeneration (FIG. 6).

Histology analysis of bleomycin-treated mice treated with the CM of chemo-activated MSC or control mice supported the flow cytometry data of BAL samples. Specifically, extensive inflammation (represented by white arrows) was observed in lungs from bleomycin-treated mice or mice treated with bleomycin and the CM from non-activated control MSCs. In contrast, lungs treated with chemo-activated MSCs exhibited minimal levels of inflammation, similar to the lungs from untreated control group (FIG. 7A). Furthermore, Sirius red staining of lungs from control bleomycin-treated mice or mice treated with CM of non-activated MSCs exhibited an increased collagen deposition (represented by white arrows) demonstrating peribronchial thickening when compared to control untreated or fibrotic lungs from mice treated with chemo-activated MSCs (FIG. 7B).

Overall, these results suggest that in mice treated with CM of chemo-activated MSCs, inflammatory process in the lungs is inhibited and therefore the tissue fibrosis is inhibited as well, and consequently the amount of lung tissue fibrosis is reduced.

Example 3

Chemotherapy Activated MSCs for Use in Treating Liver Fibrosis

Hepatocellular carcinoma, cirrhosis, and other liver pathologies still remain one of the leading causes of mortality. In most cases, alcohol abuse, unhealthy diet, viral infections, and repetitive inflammation lead to development of scar tissue spread, and extensive liver fibrosis which antecedes and promotes liver failure. This happens due to the substitution of functional hepatic tissue with fibrotic spikes which disrupt effective blood supply, induce biliary stenosis and lead to impaired liver function. However, no effective medications were developed yet to treat and reverse the damage associated with liver fibrosis. Therefore, effective therapeutic strategies are needed to preserve liver tissue structure and function and prevent fibrotic tissue formation. The method described in the current example presents an additional application of the activated cell-based therapy by inducing liver tissue regeneration and prevention of liver disease including liver fibrosis, which can further develop into liver cirrhosis and cancer.

Methods

The Generation of Chemotherapy-Activated MSC or MSC-Derived Conditioned Medium or Sctivated MSC-Derived Exosomes Murine MSCs were isolated from bone marrow aspirates and cultured in culture dishes in minimum essential medium-alpha (αMEM) supplemented with 10% FBS 1% L-glutamine, 1% sodium-pyruvate, and 1% streptomycin was used. The purification of MSCs was performed based on their adhesion abilities to plastic culture dishes. The medium was changed every 3 days until the hematopoietic cells were washed away, leaving the adhered MSCs homogenous culture. The achieved murine MSCs were expanded and passaged, while cells up to passage 10 were used for the experiments.

To generate chemotherapy-educated MSCs, cultured MSCs were exposed to gemcitabine (0-10 nM), or vehicle control for 24 hours. To generate MSC-derived CM, the chemotherapy-educated MSCs (as above) were re-seeded in a serum-free medium at a concentration of $1\times10^5$ cells/ml. After 72 hours, CM was collected.

To extract the exosome fraction from the activated MSCs, CM of chemotherapy-activated MSC was centrifugated at 20,000 g for 1 hour at 4° C. to separate microparticles and apoptotic bodies. The obtained supernatant was consequently ultracentrifuged at 110,000 g for 2 hours at 4° C. The pellet was resuspended in PBS, aliquoted, and stored at −80° C.

Induction of Murine Liver Fibrosis Model

All animal studies and animal experimental protocols are approved by the Animal Care and Use Committee of the Technion. Murine liver fibrosis model was established by a serial injection of dimethylnitrosamine (DNM), given intraperitoneally (IP), for three consecutive days, for four weeks, as was previously described in Chooi, K. F., et al., The Dimethylnitrosamine or N-Nitrosodimetilamine (DNM or NDMA) Induced Liver Fibrosis Model in the Rat. J Vis Exp, 2016(112) as well as in Cox, T. R., et al., LOX-mediated collagen crosslinking is responsible for fibrosis-enhanced metastasis. Cancer Res, 2013. 73(6): p. 1721-32. Briefly, 8-10-week-old female C57/Bl mice were administrated IP with DNM (5 mg/kg; Sigma Aldrich, Israel) or treated with vehicle control. Two weeks after treatment initiation, mice were either left untreated or injected with conditioned medium of control-MSC or chemo-activated-MSC or exosomes generated from chemo-activated MSC. The therapy was given every other day for a two-week period. When mice were sacrificed, livers were removed and processed for histological analysis and evaluation of the fibrosis grade. In parallel, a single liver lobe was processed for single cell suspension and was analyzed by flow cytometry for subsets of inflammatory cells and fibroblasts. Additional liver lobes were processed for soluble collagen content assessment.

Evaluation of Liver Fibrosis Based on Liver Physiology

To test the physiological function of the liver in mice with DNM-induced liver fibrosis, the mice were either left untreated or were injected intraperitoneally (IP, every other day, for a two week period) with the conditioned medium of chemo-activated or control MSCs or chemo-activated MSC derived exosomes. Blood was drawn from treated and control mice at the endpoint, and the levels of liver functional parameters, such as total protein, albumin, bilirubin, and specific liver enzymes including alkaline phosphatase (ALP), alanine aminotransperase (ALT), and aspartate aminotranspherase (AST) were assessed.

Evaluation of Cell Types Which Colonize Liver Using Flow Cytometry

To assess the various cell types infiltrating the liver, cells were extracted from the livers of DNM-treated or control mice. The cells were then immunostained and analyzed to define liver fibroblasts (CD90+) and various innate and adaptive immune cell populations, including T cells (CD4+ and CD8+), B cells (B220+), macrophages (CD11b+ F4/80+, CD11c±, CD206±), NK cells (NKp46+), and myeloid derived suppressor cells (MDSC; CD11b+, Ly6G±, Ly6C±). All monoclonal antibodies were purchased from BioLegend (San Diego, CA, USA) and used in accordance with the manufacturers' instructions. Sample acquisition was performed using LSR Fortessa flow analyzing system (BD Biosciences, San Jose, CA, USA) followed by analysis using the FlowJo X software (FlowJo, LLC, Ashland, OR, USA).

Histology

To evaluate the effects of the activated cell-based therapy on the progression of liver fibrosis, its tissue composition, and structure, livers were harvested from control and treated mice and fixated with 4% paraformaldehyde (PFA) solution. Paraffin-embedded liver tissues were sectioned and stained with Hematoxylin and Eosin (H&E). To assess the expression of collagen aggregation in livers and evaluate the extent of fibrosis in DNM-treated or untreated mice, the amount of soluble collagen levels was assessed using Sircol™ soluble collagen assay (Biocolor, UK). In addition, liver sections were stained with Sirius Red and analyzed for collagen deposition.

Results

Study Liver Function in Response to Chemo-Activated MSC

Figure 9A:
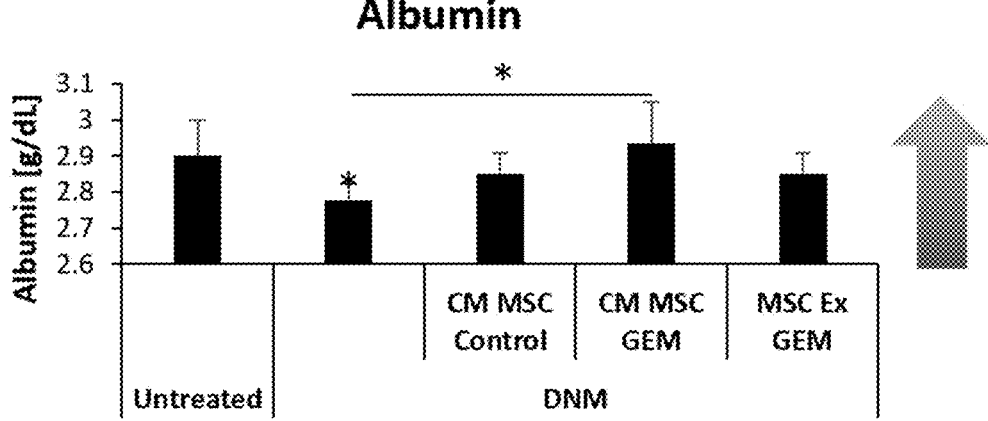
Figure 9B:
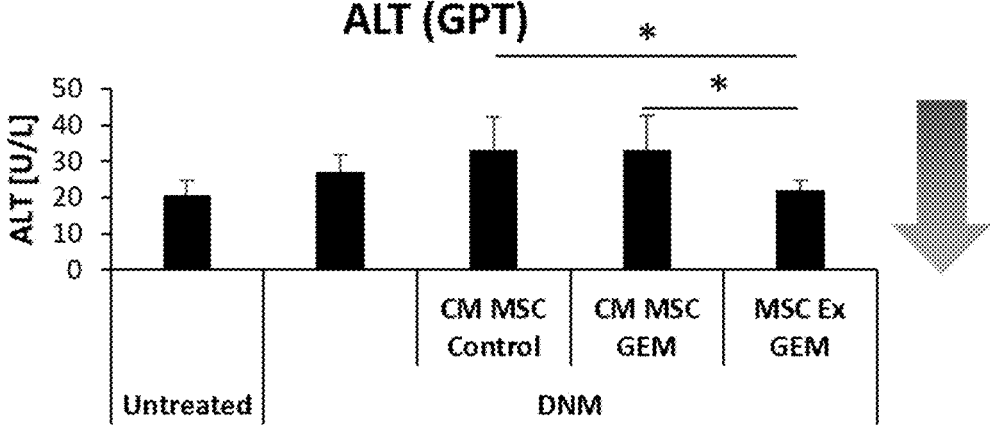
Figure 9C:
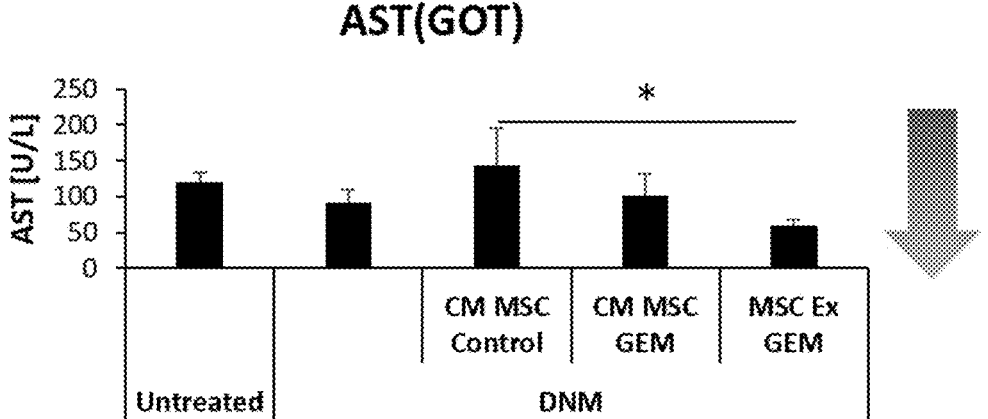
Figure 10A:
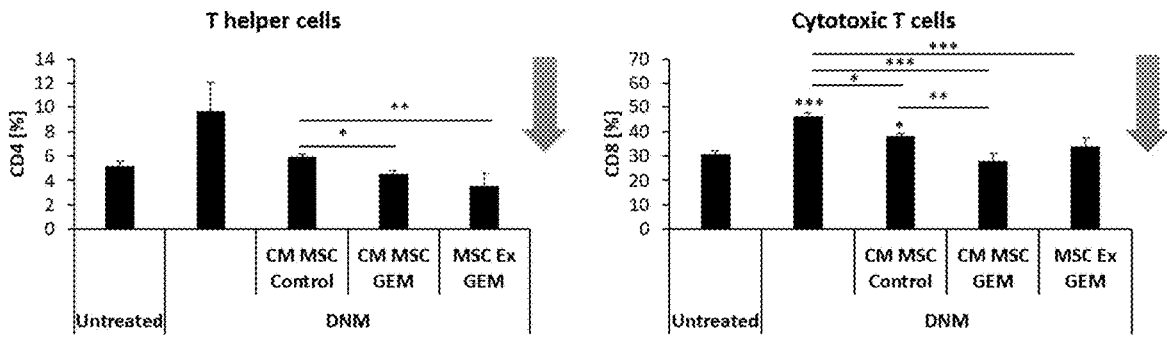
Figure 10B:
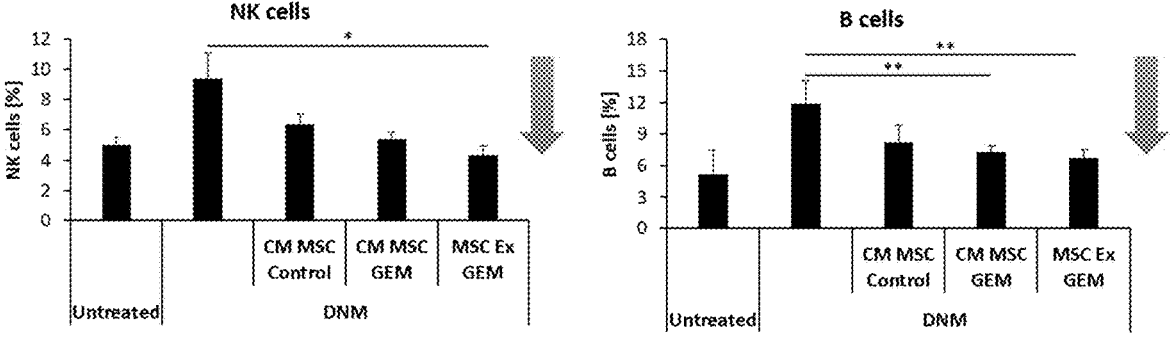
Figure 10C:
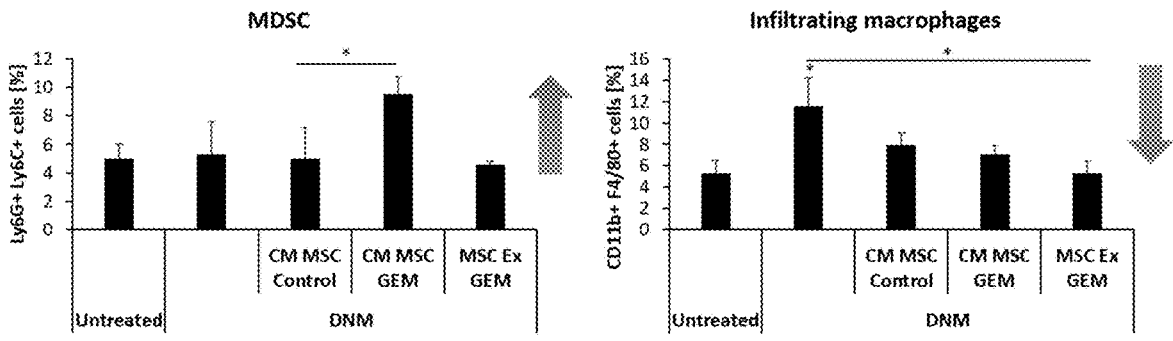
Figure 10D:
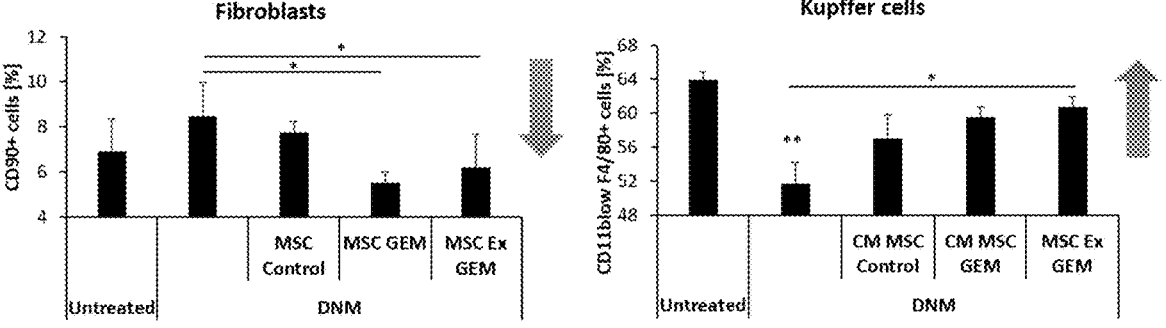

Tissue injury often results in developing of scar tissue and fibrosis, when functional tissue is massively replaced with rough connective tissue leading to an impaired physiological function. Specifically, liver fibrosis is a critical stage in liver pathology, which in most cases develop in liver cirrhosis and cancer. The exact causes for fibrotic tissue development in liver are unknown, although several factors can promote the fibrosis of liver, such as viral infections (HCV), diet, increased alcohol consumption, and genetic aberrations. In experimental animal settings, DNM, also known as NDMA, along with other chemicals is a widely used agent for induction of liver fibrosis model. Therefore, we implemented DNM-induced fibrosis model to assess the efficiency of our proposed activated cell-based therapy for preventing and healing of liver fibrosis. Specifically, 8-to-10 week old BALB/c mice were induced with liver fibrosis, by serial weekly injections of DNM. After 2 weeks, mice were treated IP (every other day, for a 2 week period) with the conditioned medium of control MSC or chemo-activated MSC or exosomes generated from chemo-activated MSC. As a control, mice were injected with PBS. Notably, neither DNM injections, nor therapy with the CM of MSCs or their exosomes resulted in severe toxicity, as measured by animal body weight. The body weight of all experimental subgroups remained normal and similar to the weight of untreated mice (FIG. 8). At endpoint, blood was analyzed for physiological function of the livers from DNM-treated mice control or those that were injected with the CM of chemo-activated MSCs. As expected, liver function was impaired in DNM-treated mice, as demonstrated by reduced albumin levels and increased levels of ALT and AST enzymes. However, mice that were treated with the conditioned medium of gemcitabine-activated MSC or their exosome-fraction showed substantial improvement in the liver function. Namely, the mice treated with CM of chemo-activated MSCs exhibited increased albumin levels and decreased liver enzymes levels, which are similar to the parameters of control untreated naïve mice (FIG. 9A-C). Furthermore, DNM-induced liver fibrosis reduced the levels of liver-resident Kupffer cells and promoted an increased influx of fibroblasts and immune cells into the liver, including T cells, B cells, NK cells, myeloid cells, and macrophages. Altogether, the elevated levels of these cells represent increased liver inflammation, which attenuates tissue regeneration and promotes fibrosis. However, treatment with the CM of activated MSCs or their exosome fraction decreased the percentage of inflammatory cells in the liver and increased the immunosuppressive myeloid derived suppressor cells, thus promoting tissue regeneration (FIG. 10A-D).

To evaluate the fibrosis grade and collagen deposition in the livers of mice treated with the CM of chemo-activated MSC or control mice, we assessed soluble collagen levels in the treated livers. Treatment with the CM of activated MSC resulted in a substantial decrease of soluble collagen, when compared to the control groups treated with DNM (FIG. 11A). Histology analysis of the livers supported the aforementioned data of the treated livers. Specifically, H&E and Sirius red staining demonstrated extensive fibrosis around the central canals, as well as in the portal areas of the DNM-treated livers (represented by white arrows). On the contrary, liver histology from mice treated with the conditioned medium of gemcitabine-activated MSC resembled the histology of livers from untreated healthy (naïve) control mice, suggesting a complete regeneration of the fibrotic tissue. As expected, treatment with our therapy given as exosomes, resulted in a similar reduction of the liver fibrosis, while the CM of control MSC did not show any significant improvement of the liver fibrosis of DNM-treated mice (FIG. 11B-D).

Overall, these results suggest that in mice treated with the CM of gemcitabine-activated MSCs liver inflammation is inhibited, which improves tissue regeneration and therefore prevents and reduces liver fibrosis, and restores healthy liver function.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for promoting tissue regeneration or organ repair of a damaged organ, in a human subject in need thereof, the method comprising: administering to said subject a pharmaceutical composition comprising an effective amount of a cultured media from a mesenchymal stem cells (MSCs) activated with gemcitabine by a step of culturing, wherein said MSCs were activated with the gemcitabine at a concentration of about 10 nM between about 10 minutes to about 72 hours, wherein said cultured media is not cytotoxic to the subject, wherein promoting tissue regeneration or organ repair of a damaged organ comprises treating fibrosis.

2. The method of claim 1, wherein said composition comprises culture media from at least 10ˆ5 of said activated MSCs.

3. The method of claim 1, wherein said tissue regeneration or organ repair of a damaged organ comprises enhanced angiogenesis, immunosuppression or both.

4. The method of claim 1, wherein said administering comprises direct administration to a tissue or organ to be repaired or regenerated or peripheral administration.

5. The method of claim 1, wherein the damaged organ is selected from the group consisting of: pancreas, breast, ovary, lung, heart, kidney, GI tract, intestine, skin, liver and brain.

6. The method of claim 1, wherein
the damaged organ is a pancreas, a lung or a liver.

7. The method of claim 6, wherein the damaged organ is a lung.

8. The method of claim 1, wherein said cultured media is conditioned media.

9. The method of claim 1, wherein said fibrosis is lung fibrosis, liver fibrosis or both.

10. The method of claim 1, wherein promoting tissue regeneration or organ repair of a damaged organ comprises initiating angiogenesis.

11. The method of claim 1, wherein promoting tissue regeneration or organ repair of a damaged organ comprises inducing immunosuppression.

12. The method of claim 1, wherein promoting tissue regeneration or organ repair of a damaged organ comprises reducing inflammation.

13. The method of claim 1, wherein said method is a method for promoting tissue regeneration.

14. The method of claim 13, wherein said tissue regeneration comprises wound healing.

15. The method of claim 1, wherein said MSCs were activated with the gemcitabine for about 24 hours.

* * * * *